US005614396A

United States Patent [19]
Bradley et al.

[11] Patent Number: 5,614,396
[45] Date of Patent: Mar. 25, 1997

[54] METHODS FOR THE GENETIC MODIFICATION OF ENDOGENOUS GENES IN ANIMAL CELLS BY HOMOLOGOUS RECOMBINATION

[75] Inventors: Allan Bradley; Ann Davis; Paul Hasty, all of Houston, Tex.

[73] Assignee: Baylor College of Medicine, Houston, Tex.

[21] Appl. No.: 200,011

[22] Filed: Feb. 22, 1994

Related U.S. Application Data

[63] Continuation of Ser. No. 3,825, Jan. 8, 1993, abandoned, which is a continuation-in-part of Ser. No. 537,458, Jun. 14, 1990, abandoned.

[51] Int. Cl.$^6$ .............................. C12N 15/00; C12N 5/00
[52] U.S. Cl. ...................... 435/172.3; 435/325; 935/71
[58] Field of Search .......................... 435/240.1, 172.3; 800/2; 935/71

[56] References Cited

U.S. PATENT DOCUMENTS

| 4,736,866 | 4/1988 | Leder et al. | 800/1 |
|---|---|---|---|
| 4,870,009 | 9/1989 | Evans et al. | 435/70 |

FOREIGN PATENT DOCUMENTS

| WO82/04443 | 12/1982 | WIPO. |
| WO87/05325 | 9/1987 | WIPO. |
| WO87/07298 | 12/1987 | WIPO. |

OTHER PUBLICATIONS

Garrick et al (1987) Biochem. Genet. 25, 391–399.
Jaenisch, R., "Transgenic Animals," *Science* 240:1468–1474 (1988).
Westphal, H., "Transgenic mammals and biotechnology," *FASEB J.* 3:117 (1989).
Lacey, M. et al., "Bovine papillomavirus genome elicits skin tumours in transgenic mice," *Nature* 322:609 (1986).
Evans, M.J. et al., "Establishment in culture of pluripotential cells from mouse embryos," *Nature* 292:154–156 (1981).
Robertson, E., In: *Current Communications in Molecular Biology*, Capecchi, M. (ed.), Cold Spring Harbor Press, Cold Spring Harbor, NY (1989), pp. 39–44 (1989).
Robertson, E.J., "Embryo–derived stem cell lines," In: Teratocarcinomas and Embryonic Stem Cells: A Practical Approach, (E. Robertson, Ed.), IRL Press, Oxford, 1987, pp. 71–112).
Martin, G.R. et al., "Isolation of a plutipotent cell line from early mouse embryos cultured in medium conitioned by teratocarcinoma stem cells," *Proc. Natl. Acad. Sci. (U.S.A.)* 78:7634–7638 (1981).
Robertson, E. et al., "Isolation, Properties, and Karyotype Analysis of Pluripotential (EK) Cell Lines from Normal and Parthenogenetic Embryos," *Cold Spring Harb. Conf. Cell Prolif.* 10:647–663 (1983).
Bradley, A. et al., "Formation of germ–line chimaeras from embryo–derived teratocarcinoma cell lines," *Nature* 309:255–256 (1984).

Stewart, C. L. et al., "Expression of foreign genes from retroviral vectors in mouse teratocarcinoma chimaeras," *EMBO J.* 4:3701–3709 (1985).
Gossler, A. et al., "Transgenesis by means of blastocyst–derived embryonic stem cell lines," *Proc. Natl. Acad. Sci. (U.S.A.)* 83:9065–9069 (1986).
Wagner, et al., "Gene Transfer into Murine Stem Cells and Mice Using Retroviral Vectors," *Cold Spring Harb. Symp. Quant. Biol.* 50:691–700 (1985).
Brinster, R.L. et al., "Targeted correction of a major histocompatibility class II Eα gene by DNA microinjected into mouse eggs," *Proc. Natl. Acad. Sci. (U.S.A.)* 86:7087–7091 (1989).
Capecchi, M.R., "The New Mouse Genetics: Altering the Genome by Gene Targeting," *Trends Genet.* 5:70–76 (1989).
Capecchi, M.R. et al., In: *Current Communications in Molecular Biology*, capecchi, M. (ed.), cold Spring Harbor Press, Cold Spring Harbor, NY (1989), pp. 45–52.
Capecchi, M.R., "Altering the Genome by Homologous Recombination," *Science* 244:1288–1292 (1989).
Doetschman, T. et al., "Targeted mutation of the HPRT gene in mouse embryonic stem cells," *Proc. Natl. Acad. Sci. (U.S.A.)* 85:8583–8587 (1988).
Thompson, S. et al., "Germ Line Transmission and Expression of Corrected HPRT Gene Produced by Gene Targeting in Embryonic Stem Cells," *Cell* 56:313–321 (1989).
Smithies, O. et al., "Insertion of DNA sequences into the human chromosomal β–globin locus by homologous recombination," *Nature* 317:230–234 (1985).
Schwartzberg, P.L. et al., "Germ–Line Transmission of a c–abl Mutation Produced by Targeted Gene Disruption in ES Cells," *Science* 246:799–803 (1989).
Zimmer, A. et al., "Production of chimaeric mice containing embryonic stem (ES) cells carrying a homoeobox Hox 1.1 allele mutated by homologous recombination," *Nature* 338:150–154 (1989).
Joyner, A.L. et al., "Production of a mutation in mouse En–2 gene by homologous recombination in embryonic stem cells," *Nature* 338:153–155 (1989).
Thomas, K.R. et al., "Site–Directed Mutagenesis by Gene Targeting in Mouse Embryo–Derived Stem Cells," *Cell* 51:503–512 (1987).
Mansour, S.L. et al., "Disruption of the proto–oncogene int–2 in moues embryo–derived stem cells: a general strategy for targeting mutations to non–selectable genes," *Nature* 336:348–352 (1988).

(List continued on next page.)

*Primary Examiner*—Deborah Crouch
*Attorney, Agent, or Firm*—Fulbright & Jaworski L.L.P.

[57] ABSTRACT

A method for producing animal cells, chimeric or transgenic non-human animals which contain a desired gene sequence inserted into a predetermined gene sequence. The method permits the production of animal cells and non-human animals which have subtle and precise modifications of gene sequence and expression relative to natural non-human animals.

32 Claims, 17 Drawing Sheets

OTHER PUBLICATIONS

Koller, B.H. et al., "Inactivation the β2–microglobulin locus in mouse embryonic stem cells by homologous recombination," *Proc. Natl. Acad. Sci. (U.S.A.)* 86:8932–8935 (1989).

Koller, B.H. et al., "Germ–line transmission of a planned alteration made in a hypoxanthine phosphoribosyltransferase gene by homologous recombination in embryonic stem cells," *Proc. Natl. Acad. Sci. (U.S.A.)* 86:8927–8931 (1989).

Zijlstra, M. et al., "Germ–line transmission of a disrupted β2–microglobulin gene produced by homologous recombination in embryonic stem cells," *Nature* 342:435–438 (1989).

Zijlstra, M. et al., "β2–Microglobulin deficient mice lack CD4–8+ cytolytic T cells," *Nature* 344:742–746 (1989).

Frohman, M. A. et al., "Cut, Paste, and Save: New Approaches to Altering Specific Genes in Mice," *Cell* 56:145–147 (1989).

Sedivy, J.M., "New Genetic Methods for Mammalian Cells," *Bio–Technol.* 6:1192–1196 (1988).

Boggs, S.S., "Targeted Gene Modification for Gene Therapy of Stem Cells," *Int. J. Cell Clon.* 8:80–96 (1990).

Evans, M.J. et al., "The Ability of EK Cells to Form Cheimeras after Selection of Clones in G418 and Some Observations on the Integration of Retroviral Vector Proviral DNA into EK Cells," *Cold Spring Harb. Symp. Quant. Biol.* 50:685–689 (1985).

Gough, N.M. et al., "LIF: a Molecule with Divergent Actions on Myeloid Leukaemic Cells and Embryonic Stem Cells," *Reprod. Fertil. Dev.* 1:281–288 (1989).

Yamamori, Y. et al., "The Cholinergic Neuronal Differentiation Factor from Heart Cells Is Identical to Leukemia Inhibitory Factor," *Science* 246:1412–1416 (1989).

Gridley, T. et al., "Insertional mutagenesis in mice,"*Trends Genet.* 3:162–166 (1987).

Bradley, A. et al., "Embryo–Derived Stem Cells: A Tool for Elucidating the Developmental Genetics of the Mouse," *Curr. Top. Devel. Bio.* 20:357–371 (1986).

Bradley, A. "Production and analysis of chimaeric mice," (In: Teratocarcinomas and Embryonic Stem *Cells: A Practical Approach*, (E.J. Robertson, Ed.), IRL Press, Oxford, 1987, pp. 113–151)).

Zimmer, A. et al., In: *Current Communications in Molecular Biology*, Capecchi, M.R. (ed.), Cold Spring Cold Spring Harbor Press, Cold Spring Harbor, NY (1989), pp. 53–58.

Thomas, B.J. et al., "Elevated Recombination Rates in Transcriptionally Active DNA," *Cell* 56:619–630 (1989).

Sambrook, J. et al., *Molecular Cloning A laboratory Manual*, Cold Spring Harbor, NY (1989), pp. 16.8–16.15 *check cite form.*

Rudolph, H. et al., "One–step gene replacement in yeast by cotransformation," *Science* 36:87–95 (1985).

Bradley et al (1992) Biotechnology 10, 534–539.

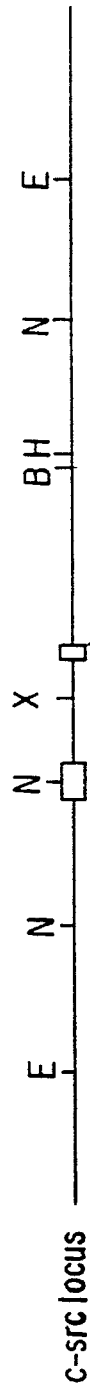
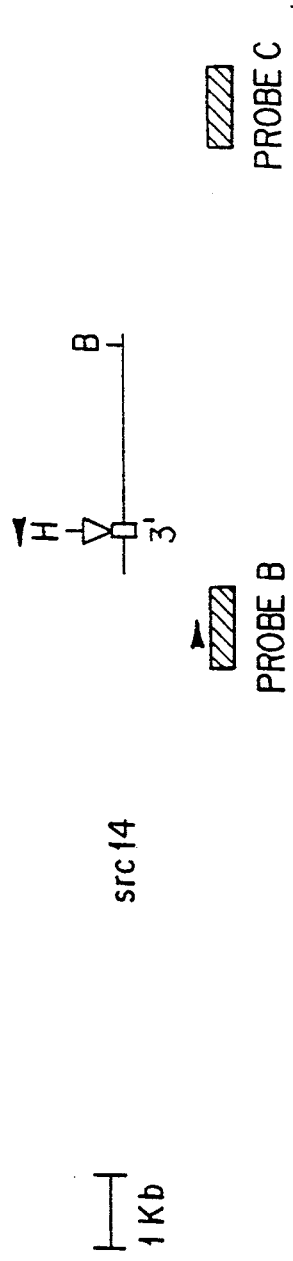
FIG. 11A
FIG. 11B
FIG. 11C

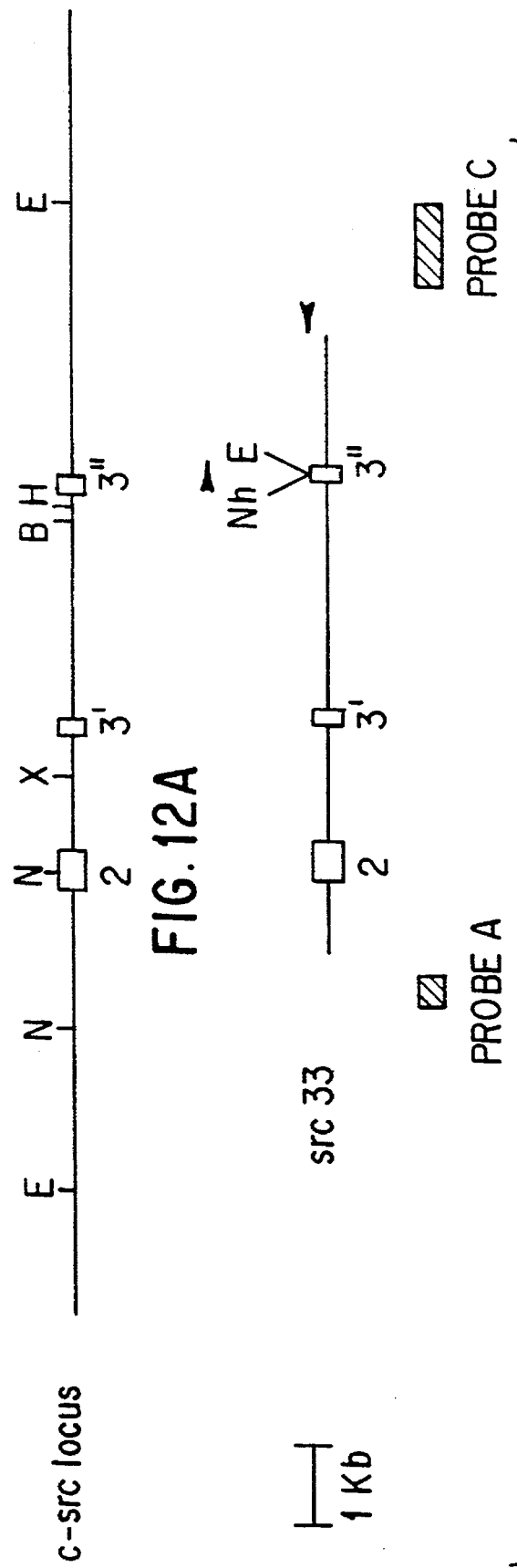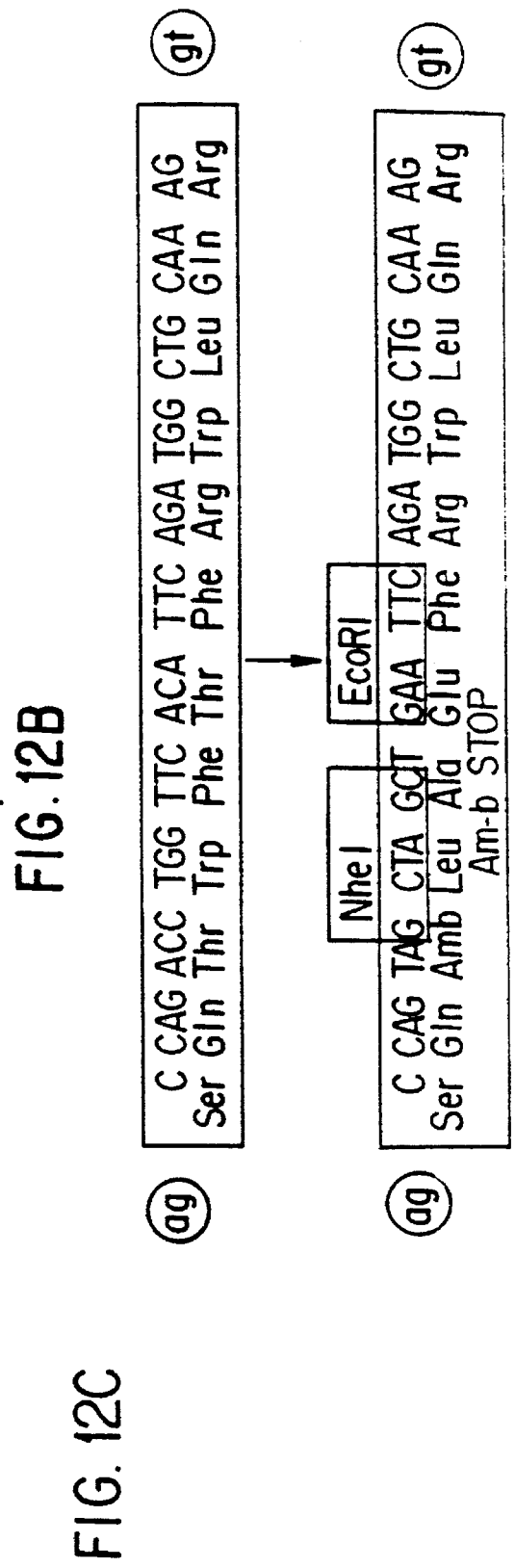
FIG. 12A
FIG. 12B
FIG. 12C

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Mus musculus
        ( B ) STRAIN: Embryonic Stem Cell ( v i i ) IMMEDIATE SOURCE:
        ( B ) CLONE: AB1; AB2

( x i ) SEQUENCE DESCRIPTION: SEQ ID NO:1:

GAGGAAGGTG GATGTCAG
        1 8

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
                ( A ) ORGANISM: c-src ( x i ) SEQUENCE DESCRIPTION: SEQ ID NO:2:

Arg Lys Val Asp Val
 1               5

( 2 ) INFORMATION FOR SEQ ID NO:3:

( i ) SEQUENCE CHARACTERISTICS:
                ( A ) LENGTH: 27 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
                ( A ) ORGANISM: Mus musculus
                ( B ) STRAIN: Embryonic stem cell ( v i i ) IMMEDIATE SOURCE:
                ( B ) CLONE: src-14

( i x ) FEATURE:
                ( A ) NAME/KEY: misc_feature
                ( B ) LOCATION: 2..25
                ( D ) OTHER INFORMATION: /product="Amino Acid Translation
                        Product"
                        / note= "Sequence is translated as:
                        RLV-(ochre)- A-(amber)-DVR"

( i x ) FEATURE:
                ( A ) NAME/KEY: misc_feature
                ( B ) LOCATION: 12..17
                ( D ) OTHER INFORMATION: /function="recognition site for
                        HinDIII endonuclease"

( x i ) SEQUENCE DESCRIPTION: SEQ ID NO:3:

GAGGAAGGTG TAAGCTTAGG ATGTCAG                                                              2 7

( 2 ) INFORMATION FOR SEQ ID NO:4:

( i ) SEQUENCE CHARACTERISTICS:
                ( A ) LENGTH: 33 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: mus musculus
                ( B ) STRAIN: Embryonic stem cell ( v i i ) IMMEDIATE SOURCE:
                ( B ) CLONE: AB1; AB2

( x i ) SEQUENCE DESCRIPTION: SEQ ID NO:4:

CCAGACCTGG TTCACATTCA GATGGCTGCA AAG                                                        3 3

( 2 ) INFORMATION FOR SEQ ID NO:5:

( i ) SEQUENCE CHARACTERISTICS:
                ( A ) LENGTH: 12 amino acids
                ( B ) TYPE: amino acid ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
            ( A ) ORGANISM: mus musculus
            ( B ) STRAIN: Embryonic Stem Cell ( v i i ) IMMEDIATE SOURCE:
            ( B ) CLONE: AB1; AB2

( x i ) SEQUENCE DESCRIPTION: SEQ ID NO:5:

Ser Gln Thr Trp Phe Thr Phe Arg Trp Leu Gln Arg
 1               5                   10

( 2 ) INFORMATION FOR SEQ ID NO:6:

( i ) SEQUENCE CHARACTERISTICS:
            ( A ) LENGTH: 33 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
            ( A ) ORGANISM: mus musculus ( v i i ) IMMEDIATE SOURCE:
            ( B ) CLONE: SRC-33

( i x ) FEATURE:
            ( A ) NAME/KEY: misc_feature
            ( B ) LOCATION: 7..12
            ( D ) OTHER INFORMATION: /function="Recognition site for
                NheI restriction endonuclease"

( i x ) FEATURE:
            ( A ) NAME/KEY: misc_feature
            ( B ) LOCATION: 14..19
            ( D ) OTHER INFORMATION: /function="recognition site for
                EcoR1 restriction endonuclease"

( i x ) FEATURE:
            ( A ) NAME/KEY: misc_feature
            ( B ) LOCATION: 2..33
            ( D ) OTHER INFORMATION: /function="Premature termination
                of translation"
                / product= "Translation Product"
                / note= "Sequence is translated as:
                SQ-(amber)- LAGFRWLQR"

( x i ) SEQUENCE DESCRIPTION: SEQ ID NO:6:

CCAGTAGCTA GCTGAATTCA GATGGCTGCA AAG                                33

( 2 ) INFORMATION FOR SEQ ID NO:7:

( i ) SEQUENCE CHARACTERISTICS:
            ( A ) LENGTH: 9 amino acids
            ( B ) TYPE: amino acid
            ( D ) TOPOLOGY: linear ( i i ) MOLECULE TYPE: peptide ( i i i ) HYPOTHETICAL: YES (iv) ANTI-SENSE: NO (v) FRAGMENT TYPE: internal (vi) ORIGINAL SOURCE:
(A) ORGANISM: mus musculus (vii) IMMEDIATE SOURCE:
(B) CLONE: src 33

(xi) SEQUENCE DESCRIPTION: SEQ ID NO:7:

Leu Ala Gly Phe Arg Trp Leu Gln Arg
1               5

METHODS FOR THE GENETIC MODIFICATION OF ENDOGENOUS GENES IN ANIMAL CELLS BY HOMOLOGOUS RECOMBINATION

CROSS-REFERENCE TO RELATED APPLICATIONS

This application is a continuation of U.S. patent application Ser. No. 08/003,825, (filed Jan. 8, 1993now abandoned), which is a continuation-in-part application of U.S. patent application Ser. No. 07/537,458, (filed on Jun. 14, 1990, now abandoned).

FIELD OF THE INVENTION

The invention is directed toward recombinant DNA technology, and more specifically, toward methods for modifying endogenous genes in a chimeric or transgenic animal or plant. The invention further pertains to the animals/plants produced through application of the method, and to the use of the method in medicine and agriculture. This invention was supported by Government funds. The Government has certain rights in this invention.

BACKGROUND OF THE INVENTION

I. Chimeric and Transgenic Animals

Recent advances in recombinant DNA and genetic technologies have made it possible to introduce and express a desired gene sequence in a recipient animal. Through the use of such methods, animals have been engineered to contain gene sequences that are not normally or naturally present in an unaltered animal. The techniques have also been used to produce animals which exhibit altered expression of naturally present gene sequences.

The animals produced through the use of these methods are known as either "chimeric" or "transgenic" animals. In a "chimeric" animal, only some of the animal's cells contain and express the introduced gene sequence, whereas other cells have been unaltered. The capacity of a chimeric animal to transmit the introduced gene sequence to its progeny depends upon whether the introduced gene sequences are present in the germ cells of the animal. Thus, only certain chimeric animals can pass along the desired gene sequence to their progeny.

In contrast, all of the cells of a "transgenic" animal contain the introduced gene sequence. Consequently, a transgenic animal is capable of transmitting the introduced gene sequence to its progeny.

II. Production of Transgenic Animals: Microinjection Methods

The most widely used method through which transgenic animals have been produced involves injecting a DNA molecule into the male pronucleus of a fertilized egg (Brinster, R. L. et al., *Cell* 27:223 (1981); Costantini, F. et al., *Nature* 294:92 (1981); Harbers, K. et al., *Nature* 293:540 (1981); Wagner, E. F. et al., *Proc. Natl. Acad. Sci.* (U.S.A.) 78:5016 (1981); Gordon, J. W. et al., *Proc. Natl. Acad. Sci.* (U.S.A.) 73:1260 (1976)).

The gene sequence being introduced need not be incorporated into any kind of self-replicating plasmid or virus (Jaenisch, R., *Science,* 240:1468–1474 (1988)). Indeed, the presence of vector DNA has been found, in many cases, to be undesirable (Hammer, R. E. et al., *Science* 235:53 (1987); Chada, K. et al., *Nature* 39:685 (1986); Kollias, G. et al., *Cell* 46:89 (1986); Shani, M., *Molec. Cell. Biol.* 6:2624 (1986); Chada, K. et al., *Nature* 314:377 (1985); Townes, T. et al., *EMBO J.* 4:1715 (1985)).

After being injected into the recipient fertilized egg, the DNA molecules are believed to recombine with one another to form extended head-to-tail concatemers. It has been proposed that such concatemers occur at sites of double-stranded DNA breaks at random sites in the egg's chromosomes, and that the concatemers are inserted and integrated into such sites (Brinster, R. L. et al., *Proc. Natl. Acad. Sci.* (U.S.A.) 82:4438 (1985)). Although it is, thus, possible for the injected DNA molecules to be incorporated at several sites within the chromosomes of the fertilized egg, in most instances, only a single site of insertion is observed (Jaenisch, R., *Science,* 240:1468–1474 (1988); Meade, H. et al. (U.S. Pat. No. 4,873,316)).

Once the DNA molecule has been injected into the fertilized egg cell, the cell is implanted into the uterus of a recipient female, and allowed to develop into an animal. Since all of the animal's cells are derived from the implanted fertilized egg, all of the cells of the resulting animal (including the germ line cells) shall contain the introduced gene sequence. If, as occurs in about 30% of events, the first cellular division occurs before the introduced gene sequence has integrated into the cell's genome, the resulting animal will be a chimeric animal.

By breeding and inbreeding such animals, it has been possible to produce heterozygous and homozygous transgenic animals. Despite any unpredictability in the formation of such transgenic animals, the animals have generally been found to be stable, and to be capable of producing offspring which retain and express the introduced gene sequence.

Since microinjection causes the injected DNA to be incorporated into the genome of the fertilized egg through a process involving the disruption and alteration of the nucleotide sequence in the chromosome of the egg at the insertion site, it has been observed to result in the alteration, disruption, or loss of function of the endogenous egg gene in which the injected DNA is inserted. Moreover, substantial alterations (deletions, duplications, rearrangements, and translocations) of the endogenous egg sequences flanking the inserted DNA have been observed (Mahon, K. A. et al., *Proc. Natl. Acad. Sci.* (U.S.A.) 85:1165 (1988); Covarrubias, Y. et al., *Proc. Natl. Acad. Sci.* (U.S.A.) 83:6020 (1986); Mark, W. et al., *Cold Spr. Harb. Symp. Quant. Biol.* 50:453 (1985)). Indeed, lethal mutations or gross morphological abnormalities have been observed (Jaenisch, R., *Science* 240:1468–1474 (1988); First, N. L. et al., *Amer. Meat Sci. Assn. 39th Reciprocal Meat Conf.* 39:41 (1986))).

Significantly, it has been observed that even if the desired gene sequence of the microinjected DNA molecule is one that is naturally found in the recipient egg's genome, integration of the desired gene sequence rarely occurs at the site of the natural gene (Brinster, R. L. et al., *Proc. Natl. Acad. Sci.* (U.S.A.) 86:7087–7091 (1989)). Moreover, introduction of the desired gene sequence does not generally alter the sequence of the originally present egg gene.

Although the site in the fertilized egg's genome into which the injected DNA ultimately integrates cannot be predetermined, it is possible to control the expression of the desired gene sequence such that, in the animal, expression of the sequence will occur in an organ or tissue specific manner (reviewed by Westphal, H., *FASEB J.* 3:117 (1989); Jaenisch, R., *Science* 240:1468–1474 (1988)).

The success rate for producing transgenic animals is greatest in mice. Approximately 25% of fertilized mouse eggs into which DNA has been injected, and which have been implanted in a female, will become transgenic mice. A lower rate has been thus far achieved with rabbits, sheep, cattle, and pigs (Jaenisch, R., *Science* 240:1468–1474 (1988); Hammer, R. E. et al., *J. Animal. Sci.* 63:269 (1986); Hammer, R. E. et al., *Nature* 315:680 (1985); Wagner, T. E. et al., *Theriogenology* 21:29 (1984)). The lower rate may reflect greater familiarity with the mouse as a genetic system, or may reflect the difficulty of visualizing the male pronucleus of the fertilized eggs of many farm animals (Wagner, T. E. et al., *Theriogenology* 21:29 (1984)).

Thus, the production of transgenic animals by microinjection of DNA suffers from at least two major drawbacks. First, it can be accomplished only during the single-cell stage of an animal's life. Second, it requires the disruption of the natural sequence of the DNA, and thus is often mutagenic or teratogenic (Gridley, T. et al., *Trends Genet.* 3:162 (1987)).

III. Production of Chimeric and Transgenic Animals: Recombinant Vital and Retroviral Methods Chimeric and transgenic animals may also be produced using recombinant viral or retroviral techniques in which the gene sequence is introduced into an animal at a multicell stage. In such methods, the desired gene sequence is introduced into a virus or retrovirus. Cells which are infected with the virus acquire the introduced gene sequence. If the virus or retrovirus infects every cell of the animal, then the method results in the production of a transgenic animal. If, however, the virus infects only some of the animal's cells, then a chimeric animal is produced.

The general advantage of viral or retroviral methods of producing transgenic animals over those methods which involve the microinjection of non-replicating DNA, is that it is not necessary to perform the genetic manipulations at a single cell stage. Moreover, infection is a highly efficient means for introducing the DNA into a desired cell.

Recombinant retroviral methods for producing chimeric or transgenic animals have the advantage that retroviruses integrate into a host's genome in a precise manner, resulting generally in the presence of only a single integrated retrovirus (although multiple insertions may occur). Rearrangements of the host chromosome at the site of integration are, in general, limited to minor deletions (Jaenisch, R., *Science* 240:1468–1474 (1988); see also, Varmus, H., In: *RNA Tumor Viruses* (Weiss, R. et al., Eds.), Cold Spring Harbor Press, Cold Spring Harbor, N.Y., pp. 369–512 (1982)). The method is, however, as mutagenic as microinjection methods.

Chimeric animals have, for example, been produced by incorporating a desired gene sequence into a virus (such as bovine papilloma virus or polyoma) which is capable of infecting the cells of a host animal. Upon infection, the virus can be maintained in an infected cell as an extrachromosomal episome (Elbrecht, A. et al., *Molec. Cell. Biol.* 7:1276 (1987); Lacey, M. et al., *Nature* 322:609 (1986); Leopold, P. et al., *Cell* 51:885 (1987)). Although this method decreases the mutagenic nature of chimeric/transgenic animal formation, it does so by decreasing germ line stability, and increasing oncogenicity.

Pluripotent embryonic stem cells (referred to as "ES" cells) are cells which may be obtained from embryos until the early post-implantation stage of embryogenesis. The cells may be propagated in culture, and are able to differentiate either in vitro or in vivo upon implantation into a mouse as a tumor. ES cells have a normal karyotype (Evans, M. J. et al., *Nature* 292:154–156 (1981); Martin, G. R. et al., *Proc. Natl. Acad. Sci.* (U.S.A.) 78:7634–7638 (1981)).

Upon injection into a blastocyst of a developing embryo, ES cells will proliferate and differentiate, thus resulting in the production of a chimeric animal. ES cells are capable of colonizing both the somatic and germ-line lineages of such a chimeric animal (Robertson, E. et al. *Cold Spring Harb. Conf. Cell Prolif.* 10:647–663 (1983); Bradley A. et al., *Nature* 309:255–256 (1984); Bradley, A. et al., *Curr. Top, Devel. Biol.* 20:357–371 (1986); Wagner, E. F. et al., *Cold Spring Harb. Symp. Quant. Biol.* 50:691–700 (1985); (all of which references are incorporated herein by reference).

In this method, ES cells are cultured in vitro, and infected with a viral or retroviral vector containing the gene sequence of interest. Chimeric animals generated with retroviral vectors have been found to have germ cells which either lack the introduced gene sequence, or contain the introduced sequence but lack the capacity to produce progeny cells capable of expressing the introduced sequence (Evans, M. J. et al., Cold Spring Harb. Symp., Quant. Biol. 50:685–689 (1985); Stewart, C. L. et al., *EMBO J.* 4:3701–3709 (1985); Robertson, L. et al., *Nature* (1986); which references are incorporated herein by reference).

Because ES cells may be propagated in vitro, it is possible to manipulate such cells using the techniques of somatic cell genetics. Thus, it is possible to select ES cells which carry mutations (such as in the hprt gene (encoding hypoxanthine phosphoribosyl transferase) (Hooper, M. et al., *Nature* 326:292–295 (1987); Kuehn, M. R. et al., *Nature* 326:295–298 (1987)). Such selected cells can then be used to produce chimeric or transgenic mice which fail to express an active HPRT enzyme, and thus provide animal models for diseases (such as the Lesch-Nyhan syndrome which is characterized by an HPRT deficiency) (Doetschman, T. et al., *Proc. Natl. Acad. Sci.* (U.S.A.) 85:8583–8587 (1988)).

As indicated above, it is possible to generate a transgenic animal from a chimeric animal (whose germ line cells contain the introduced gene sequence) by inbreeding.

The above-described methods permit one to screen for the desired genetic alteration prior to introducing the transfected ES cells into the blastocyst. One drawback of these methods, however, is the inability to control the site or nature of the integration of the vector.

IV. Production of Chimeric and Transgenic Animals: Plasmid Methods

The inherent drawbacks of the above-described methods for producing chimeric and transgenic animals have caused researchers to attempt to identify additional methods through which such animals could be produced.

Gossler, A. et al., for example, have described the use of a plasmid vector which had been modified to contain the gene for neomycin phosphotransferase (nptII gene) to transfect ES cells in culture. The presence of the nptII gene conferred resistance to the antibiotic G418 to ES cells that had been infected by the plasmid (Gossler, A. et al., *Proc. Natl. Acad, Sci. (U.S.A.)* 83:9065–9069 (1986), which reference is incorporated herein by reference). The chimeric animals which received the plasmid and which became resistant to G418, were found to have integrated the vector into their chromosomes. Takahashi, Y. et al. have described the use of a plasmid to produce chimeric mice cells which expressed an avian crystallin gene (*Development*

102:258–269 (1988), incorporated herein by reference). The avian gene was incorporated into a plasmid which contained the nptII gene. Resulting chimeric animals were found to express the avian gene.

Introduction of Gene Sequences into Somatic Cells

DNA has been introduced into somatic cells to produce variant cell lines. hprt-deficient Chinese hamster ovary (CHO) cells have been transformed with the CHO hprt gene in order to produce a prototrophic cell line (Graf, L. H. et al., *Somat. Cell Genet.* 5:1031–1044 (1979)). Folger et al. examined the fate of a thymidine kinase gene (tk gene) which had been microinjected into the nuclei of cultured mammalian cells. Recipient cells were found to contain from 1 to 100 copies of the introduced gene sequence integrated as concatemers at one or a few sites in the cellular genome (Folger, K. R. et al., *Molec. Cell. Biol.* 2:1372–1387 (1982)). DNA-mediated transformation of an RNA polymerase II gene into Syrian hamster cells has also been reported (Ingles, C. et al., *Molec. Cell. Biol.* 2:666–673 (1982)).

Plasmids conferring host neomycin resistance and guanosine phosphotransferase activity have been transfected into Chinese hamster ovary cells to generate novel cell lines (Robson, C. N. et al., *Mutat. Res.* 163:201–208 (1986)).

VI. Chimeric or Transgenic Plants

Extensive progress has been made in recent years in the fields of plant cell genetics and gene technology. For many genera of plants, protoplast regeneration techniques can be used to regenerate a plant from a single cell (Friedt, W. et al. *Prog. Botany* 49:192–215 (1987); Brunold, C. et al., *Molec. Gen. Genet.* 208:469–473 (1987); Durand, J. et al., *Plant Sci.* 62:263–272 (1989) which references are incorporated herein by reference).

Several methods can be used to deliver and express a foreign gene into a plant cell. The most widely used method employs cloning the desired gene sequence into the Ti plasmid of the soil bacterium *A. tumorifaciens* (Komari, T. et al., *J. Bacteriol.* 166:88–94 (1986); Czako, M. et al., *Plant Mol. Biol.* 6:101–109 (1986); Jones, J. D. G. et. al., *EMBO J.* 4:2411–2418 (1985); Shahin, E. A. et al., *Theor. Appl. Genet.* 73:164–169 (1986)). The frequency of transformation may be as high as 70%, depending upon the type of plant used (Friedt, W. et al. *Prog. Botany* 49:192–215 (1987)).

Plant viruses have also been exploited as vectors for the delivery and expression of foreign genes in plants. The cauliflower mosaic virus (Brisson, N. et al., *Nature* 340:511–514 (1984) has been particularly useful for this purpose (Shah, D. M. et al., *Science* 233:478–481 (1986); Shewmaker, C. K. et al., *Virol.* 140:281–288 (1985). Vectors have also been prepared from derivatives of RNA viruses (French, R. et al., *Science* 231:1294–1297 (1986).

Techniques of microinjection (Crossway, A. et al., *Molec. Gen. Genet.* 202:179–185 (1986); Potrykus, I. et al., *Molec. Gen. Genet.* 199:169–177 (1985)), have been used to accomplish the direct transfer of gene sequences into plant cells. Transformation with a plasmid capable of site specific recombination has been used to introduce gene sequences into *Aspergillus* (May, G. S., *J. Cell Biol.* 109:2267–2274 (1989); which reference is incorporated herein by reference).

Electroporation has been identified as a method for introducing DNA into plant cells (Fromm, M. E., et al., *Proc. Natl. Acad. Sci.* (U.S.A) 82:5824–5828 (1985); Fromm, M. E. et al., *Nature* 319:791–793 (1986); Morikawa, H. et al., *Gene* 41:121–124 (1986); Langridge, W. H. R. et al., *Theor. Appl. Genet,* 67:443–455 (1984)).

Gross genetic mutations can be produced in plant cells using transposable elements (Saedler, H. et al., *EMBO J.* 4:585–590 (1985); Peterson, P. A., *BioEssays* 3:199–204 (1985)). Such elements can initiate chromosomal rearrangements, insertions, duplications, deletions, etc. Chimeric plants can be regenerated from such cells using the procedures described above.

A major deficiency of present methods for gene manipulation in plants is the difficulty of selecting the desired recombinant cell (Brunold, C. et al., *Molec. Gen. Genet.* 208:469–473 (1987)). In an attempt to address this deficiency, kanamycin resistance and nitrate reductase deficiency have been used as selectable markers (Brunold, C. et al., *Molec. Gen. Genet.* 208:469–473 (1987)).

VII. Conclusions

The application of the above-described technologies has the potential to produce types of plants and animals which cannot be produced through classical genetics. For example, animals can be produced which suffer from human diseases (such as AIDS, diabetes, cancer, etc.), and may be valuable in elucidating therapies for such diseases. Chimeric and transgenic plants and animals have substantial use as probes of natural gene expression. When applied to livestock and food crops, the technologies have the potential of yielding improved food, fiber, etc.

Despite the successes of the above-described techniques, a method for producing chimeric or transgenic plants and animals which was less mutagenic, and which would permit defined, specific, and delicate manipulation of the inserted gene sequence at a specific chromosomal location would be highly desirable.

BRIEF DESCRIPTION OF THE FIGURES

FIG. 1 illustrates the use of replacement vectors and insertion vectors in gene targeting.

FIG. 2 is a diagrammatical representation of a DNA molecule which has a region of heterology located at a proposed insertion site. In FIG. 2C, the normal BamHI site of the vector has been changed to an NheI site and the normal EcoRI site of the vector has been changed to a BamHI site. The vector is, linearized with XhoI.

FIG. 4 is a diagrammatical representation of the mechanism through which a large gene may be introduced into a chromosomal gene sequence so as to place the gene under the transcriptional control of a heterologous promoter (for example, to place a human gene under the control of a mouse gene). The first step is additive and the second is a replacement event.

FIG. 11 illustrates the use of the invention to introduce insertions into the sequence of a desired gene of a cell. FIG. 11A is a diagram of the c-src locus showing relevant restriction sites (E=EcoRI; N=NcoI; X=XhoI; H=HindIII; B=BamHI; Nh=NheI). FIG. 11B illustrates the src 14 vector used to introduce mutations into the c-src locus; FIG. 11C illustrates the subtle mutation introduced through the use of this vector (SEQ ID NO:1 (encoding SEQ ID NO:2) into SEQ ID NO:3).

FIG. 12 illustrates the use of the invention to introduce substitutions into the sequence of a desired gene of a cell. FIG. 12A is a diagram of the c-src locus showing relevant restriction sites (E=EcoRI; N=NcoI; X=XhoI; H=HindIII; B=BamHI; Nh=NheI). FIG. 12B illustrates the src 33 vector used to introduce mutations into the c-src locus; FIG. 12C illustrates the subtle mutation introduced through the use of this vector (SEQ ID NO:4 (encoding SEQ ID NO:5) into SEQ ID NO:6 (encoding SEQ ID NO:7).

SUMMARY OF THE INVENTION

Figure 1A:
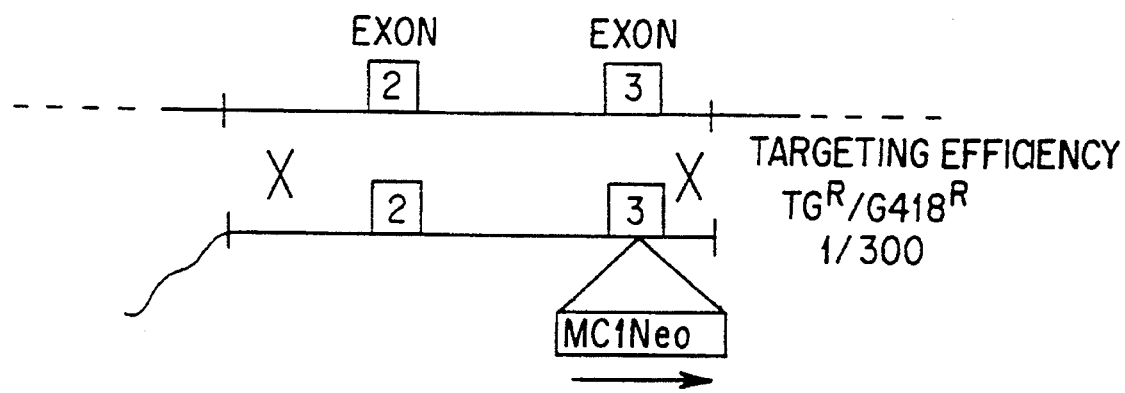
FIG. 1A is a diagrammatical representation of the use of a replacement vector in gene targeting.

The present invention provides a method for obtaining a desired animal or non-fungal plant cell which contains a predefined, specific and desired alteration in its genome. The invention further pertains to the non-human animals and plants which may be produced from such cells. The invention additionally pertains to the use of such non-human animals and plants, and their progeny in research, medicine, and agriculture.

In detail, the invention provides a method for obtaining a desired animal or non-fungal plant cell which contains a desired non-selectable gene sequence inserted within a predetermined gene sequence of the cell's genome, which method comprises:

A. incubating a precursor cell with a DNA molecule containing the desired non-selectable gene sequence, wherein the DNA molecule additionally contains two regions of homology which flank the desired gene sequence, and which are sufficient to permit the desired gene sequence to undergo homologous recombination with the predetermined gene sequence of the genome of the precursor cell;

B. causing the DNA molecule to be introduced into the precursor cell;

C. permitting the introduced DNA molecule to undergo homologous recombination with the predetermined gene sequence of the genome of the precursor cell to thereby produce the desired cell wherein the desired non-selectable gene sequence has been inserted into the predetermined gene sequence; and D. recovering the desired cell.

The invention further includes the embodiments of the above-described method wherein the DNA molecule contains a detectable marker gene sequence, and/or wherein the DNA molecule is introduced into the precursor cell by subjecting the precursor cell and the DNA molecule to electroporation (especially wherein in step B, the precursor cell is simultaneously subjected to electroporation with a second DNA molecule, the second DNA molecule containing a detectable marker gene sequence).

The invention further includes the embodiments of the above-described method wherein the desired cell is a non-fungal plant cell, a somatic animal cell (especially one selected from the group consisting of a chicken, a mouse, a rat, a hamster, a rabbit, a sheep, a goat, a fish, a pig, a cow or bull, a non-human primate and a human), a pluripotent animal cell (especially one selected from the group consisting of a chicken, a mouse, a rat, a hamster, a rabbit, a sheep, a goat, a fish, a pig, a cow or bull, and a non-human primate). The invention includes with the embodiment wherein the pluripotent cell is an embryonic stem cell.

The invention also includes the embodiments of the above-described methods wherein the desired gene sequence is substantially homologous to the predetermined gene sequence of the precursor cell and/or wherein the desired gene sequence is an analog (and especially a human analog) of the predetermined sequence of the precursor cell.

The invention also includes the embodiment wherein the desired gene sequence encodes a protein selected from the group consisting of: a hormone, an immunoglobulin, a receptor molecule, a ligand of a receptor molecule, and an enzyme.

The invention also includes a non-fungal plant cell which contains an introduced recombinant DNA molecule containing a desired gene sequence, the desired gene sequence being flanked by regions of homology which are sufficient to permit the desired gene sequence to undergo homologous recombination with a predetermined gene sequence of the genome of the cell.

The invention also includes a non-human animal cell which contains an introduced recombinant DNA molecule containing a desired gene sequence, the desired gene sequence being flanked by regions of homology which are sufficient to permit the desired gene sequence to undergo homologous recombination with a predetermined gene sequence of the genome of the cell.

The invention also includes the desired cell produced by any of the above-described methods.

The invention also includes a non-human animal containing a cell derived from the above-described desired cell, or a descendant thereof, wherein the animal is either a chimeric or a transgenic animal, and particularly includes the embodiment wherein the non-human animal and the desired cell are of the same species, and wherein the species is selected from the group consisting of: a chicken, a mouse, a rat, a hamster, a rabbit, a sheep, a goat, a fish, a pig, a cow or bull, and a non-human primate.

The invention also includes a non-fungal plant containing a cell derived from the above-described desired non-fungal plant cell, wherein said non-fungal plant is either a chimeric or a transgenic plant.

The invention also includes a method of gene therapy which comprises introducing to a recipient in need of such therapy, a desired non-selectable gene sequence, the method comprising:

A. providing to the recipient an effective amount of a DNA molecule containing the desired non-selectable gene sequence, wherein the DNA molecule additionally contains two regions of homology which flank the desired gene sequence, and which are sufficient to permit the desired gene sequence to undergo homologous recombination with a predetermined gene sequence present in a precursor cell of the recipient;

B. permitting the DNA molecule to be introduced into the precursor cell;

C. permitting the introduced DNA molecule to undergo homologous recombination with the predetermined gene sequence of the genome of the precursor cell to thereby produce a desired cell wherein the desired non-selectable gene sequence has been inserted into the predetermined gene sequence; and wherein the presence or expression of the introduced gene sequence in the cell of the recipient comprises the gene therapy.

In particular, the invention includes the embodiments of the above-stated method wherein the recipient is a non-fungal plant, or a human or a non-human animal (particularly a non-human animal is selected from the group consisting of: a chicken, a mouse, a rat, a hamster, a rabbit, a sheep, a goat, a fish, a pig, a cow or bull, a non-human primate and a human).

The invention also provides a method for obtaining a desired animal or non-fungal plant cell which contains a desired non-selectable gene sequence inserted within a predetermined gene sequence of the cell's genome, which method comprises:

A. incubating a precursor cell under non-selective culture conditions, or under a first set of selective culture conditions, with a DNA molecule containing:

i) the desired non-selectable gene sequence, wherein the DNA molecule additionally contains two regions of homology which flank the desired gene sequence, and which are sufficient to permit the desired gene sequence to undergo homologous recombination with the predetermined gene sequence of the genome of the precursor cell; and ii) a selectable gene sequence whose presence or expression in the cell can be selected for by culturing the cells under the first set of selective culture conditions, and whose presence or expression in the cell can be selected against by culturing the cells under a second set of selective culture conditions;

B. permitting the DNA molecule to be introduced into the precursor cell;

C. permitting the introduced DNA molecule to undergo homologous recombination with the predetermined gene sequence of the genome of the precursor cell to thereby produce the desired cell wherein the desired non-selectable gene sequence has been inserted into the predetermined gene sequence; and D. recovering the desired cell by culturing the cell under the first set of selective culture conditions, by then permitting the cell to undergo intrachromosomal recombination under non-selective culture conditions, and by then incubating the cell under the second set of selective culture conditions.

The invention also includes the embodiment wherein the cell is deficient in an HPRT, APRT, or TK enzyme, and wherein the selectable gene sequence expresses an active HPRT, APRT, or TK enzyme, and wherein the first set of selective culture conditions comprises incubation of the cell under conditions in which the presence of an active HPRT, APRT, or TK enzyme in the cell is required for growth, and wherein the second set of selective culture conditions comprises incubation of the cell under conditions in which the absence of an active HPRT, APRT, or TK enzyme in the cell is required for growth.

DESCRIPTION OF THE PREFERRED EMBODIMENTS

The present invention concerns a method for introducing DNA into the genome of a recipient plant or animal cell. The method may be used to introduce such DNA into germ line cells of animals (especially, rodents (i.e. mouse, rat, hamster, etc.), rabbits, sheep, goats, fish, pigs, cattle and non-human primates) in order to produce chimeric or transgenic animals. The methods may also be used to introduce DNA into plant cells which can then be manipulated in order to produce chimeric or transgenic plants.

Alternatively, the method may be used to alter the somatic cells of an animal (including humans) or a plant. The plants and plant cells which may be manipulated through application of the disclosed method include all multicellular, higher (i.e. non-fungal or non-yeast) plants.

I. Homologous Recombination

The present invention provides a method for introducing a desired gene sequence into a plant or animal cell. Thus, it is capable of producing chimeric or transgenic plants and animals having defined, and specific, gene alterations.

An understanding of the process of homologous recombination (Watson, J. D., *In: Molecular Biology of the Gene,* 3rd Ed., W. A. Benjamin, Inc., Menlo Park, Calif. (1977), which reference is incorporated herein by reference) is desirable in order to fully appreciate the present invention.

In brief, homologous recombination is a well-studied natural cellular process which results in the scission of two nucleic acid molecules having identical or substantially similar sequences (i.e. "homologous"), and the ligation of the two molecules such that one region of each initially present molecule is now ligated to a region of the other initially present molecule (Sedivy, J. M., *Bio-Technol.* 6:1192–1196 (1988), which reference is incorporated herein by reference).

Homologous recombination is, thus, a sequence specific process by which cells can transfer a "region" of DNA from one DNA molecule to another. As used herein, a "region" of DNA is intended to generally refer to any nucleic acid molecule. The region may be of any length from a single base to a substantial fragment of a chromosome.

For homologous recombination to occur between two DNA molecules, the molecules must possess a "region of homology" with respect to one another. Such a region of homology must be at least two base pairs long. Two DNA molecules possess such a "region of homology" when one contains a region whose sequence is so similar to a region in the second molecule that homologous recombination can occur.

Recombination is catalyzed by enzymes which are naturally present in both prokaryotic and eukaryotic cells. The transfer of a region of DNA may be envisioned as occurring through a multi-step process.

If either of the two participant molecules is a circular molecule, then the above recombination event results in the integration of the circular molecule into the other participant.

Importantly, if a particular region is flanked by regions of homology (which may be the same, but are preferably different), then two recombinational events may occur, and result in the exchange of a region of DNA between two DNA molecules. Recombination may be "reciprocal," and thus results in an exchange of DNA regions between two recombining DNA molecules. Alternatively, it may be "nonreciprocal," (also referred to as "gene conversion") and result in both recombining nucleic acid molecules having the same nucleotide sequence. There are no constraints regarding the size or sequence of the region which is exchanged in a two-event recombinational exchange.

The frequency of recombination between two DNA molecules may be enhanced by treating the introduced DNA with agents which stimulate recombination. Examples of such agents include trimethylpsoralen, UV light, etc.

II. Production of Chimeric and Transgenic Animals: Gene Targeting Methods

One approach to producing animals having defined and specific genetic alterations has used homologous recombination to control the site of integration of an introduced marker gene sequence in tumor cells and in fusions between diploid human fibroblast and tetraploid mouse erythroleukemia cells (Smithies, O. et al., *Nature* 317:230-234 (1985)).

This approach was further exploited by Thomas, K. R., and co-workers, who described a general method, known as "gene targeting," for targeting mutations to a preselected, desired gene sequence of an ES cell in order to produce a transgenic animal (Mansour, S. L. et al., *Nature* 336:348-352 (1988); Capecchi, M. R. *Trends Genet.* 5:70-76 (1989); Capecchi, M. R. et al., In: *Current Communications in Molecular Biology*, Capecchi, M. R. (ed.), Cold Spring Harbor Press, Cold Spring Harbor, N.Y. (1989), pp. 45-52, which references are incorporated herein by reference).

Gene targeting has been used to produce chimeric and transgenic mice in which an nptII gene has been inserted into the $\beta_2$-microglobulin locus (Koller, B. H. et al., *Proc. Natl. Acad. Sci.* (U.S.A,) 86:8932-8935 (1989); Zijlstra, M. et al., *Nature* 342:435-438 (1989); Zijlstra, M. et al., *Nature* 344:742-746 (1989); DeChiaba et al., *Nature* 345:78-80 (1990)). similar experiments have enabled the production of chimeric and transgenic animals having an c-abl which has been disrupted by the insertion of an nptII gene (Schwartzberg, P. L. et al., *Science* 246:799-803 (1989)). The technique has been used to produce chimerio mice in which the en-2 gene has been disrupted by the insertion of an nptII gene (Joyner, A. L. et al., *Nature* 338:153-155 (1989)).

Gene targeting has also been used to correct an hprt deficiency in an hprt ES cell line. Cells corrected of the deficiency were used to produce chimeric animals. Significantly, all of the corrected cells exhibited gross disruption of the regions flanking the hprt locus; all of the cells tested were found to contain at least one copy of the vector used to correct the deficiency, integrated at the hprt locus (Thompson, S. et al., *Cell* 56:313-321 (1989); Koller, B. H. et. al., *Proc. Natl. Acad. Sci.* (U.S.A.) 86:8927-8931 (1989)).

In order to utilize the "gene targeting" method, the gene of interest must have been previously cloned, and the intron-exon boundaries determined. The method results in the insertion of a marker gene (i.e. the nptII gene) into a translated region of a particular gene of interest. Thus, use of the gene targeting method results in the gross destruction of the gene of interest.

Recently, chimeric mice carrying the homeobox hox 1.1 allele have been produced using a modification of the gene targeting method (Zimmer, A. et al., *Nature* 338:150-154 (1989). In this modification, the integration of vector sequences was avoided by microinjecting ES cells with linear DNA containing only a portion of the box 1.1 allele, without any accompanying vector sequences. The DNA was found to cause the gene conversion of the cellular box allele. Selection was not used to facilitate the recovery of the "converted" ES cells, which were identified using the polymerase chain reaction ("PCR"). Approximately 50% of cells which had been clonally purified from "converted" cells were found to contain the introduced hox 1.1 allele, suggesting to Zimmer, A. et al. either chromosomal instability or contamination of sample. None of the chimeric mice were found to be able to transmit the "converted" gene to their progeny (Zimmer, A. et al., In: *Current Communications in Molecular Biology*, Capecchi, M. R. (ed.), Cold Spring Harbor Press, Cold Spring Harbor, N.Y. (1989), pp. 53-58).

The use of the gene targeting method is illustrated in FIG. 1A. In that figure, a gene construct is produced in which the nptII gene is inserted into an exon (designated region "3") of a sequence of the hprt gene. The construct is then permitted to undergo recombination with the hprt gene of a cell. Such recombination results in the replacement of the exon 3 sequence of the cell with the disrupted exon 3 - nptII sequence of the construct. Significantly, as illustrated in FIG. 1A, the use of gene targeting to alter a gene of a cell results in the formation of a gross alteration in the sequence of that gene. As indicated in FIG. 1A, the efficiency of gene targeting is approximately 1/300.

III. Production of Chimerio and Transgenic Animals: Use of Insertion Vectors

In contrast to the above-described methods, the present invention is capable of producing subtle, precise, and predetermined mutations in the sequence of a desired gene of a cell. The present invention has several embodiments, the simplest of which is illustrated in FIG. 1B.

Figure 1B:
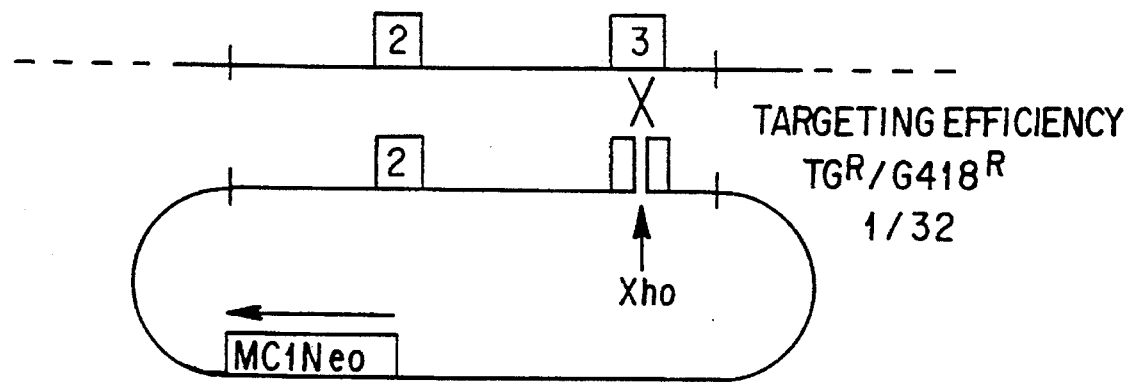
FIG. 1B illustrates the use of an insertion vector to produce subtle mutations in a desired gene sequence.

As shown in FIG. 1B, an insertion vector is used to mutate the nucleotide sequence of the hprt gene. The use of this vector type in combination with a second selectable reversion event prevents the disruption of the chromosome by the nptII gene or by the vector sequences. Thus, gross distortions of the recipient chromosome are avoided by the present invention. Moreover, the efficiency of the gene targeting was substantially improved (i.e. 1/32 as opposed to 1/300).

The DNA molecule(s) which are to be introduced into the recipient cell preferably contains a region of homology with a region of the cellular genome. In a preferred embodiment, the DNA molecule will contain two regions of homology with the genome (both chromosomal and episomal) of the pluripotent cell. These regions of homology will preferably flank a "desired gene sequence" whose incorporation into the cellular genome is desired. As stated above, the regions of homology may be of any size greater than two bases long. Most preferably, the regions of homology will be greater than 10 bases long.

The DNA molecule(s) may be single stranded, but are preferably double stranded. The DNA molecule(s) may be introduced to the cell as one or more RNA molecules which may be converted to DNA by reverse transcriptase or by other means. Preferably, the DNA molecule will be double stranded linear molecule. In the best mode for conducting the invention, such a molecule is obtained by cleaving a closed covalent circular molecule to form a linear molecule. Preferably, a restriction endonuclease capable of cleaving the molecule at a single site to produce either a blunt end or staggered end linear molecule is employed. Most preferably, the nucleotides on each side of this restriction site will comprise at least a portion of the preferred two regions of homology between the DNA molecule being introduced and the cellular genome.

The invention thus provides a method for introducing the "desired gene sequence" into the genome of an animal or plant at a specific chromosomal location. The "desired gene sequence" may be of any length, and have any nucleotide sequence. It may comprise one or more gene sequences which encode complete proteins, fragments of such gene sequences, regulatory sequences, etc. Significantly, the desired gene sequence may differ only slightly from a native gene of the recipient cell (for example, it may contain single, or multiple base alterations, insertions or deletions relative to the native gene). The use of such desired gene sequences will permit one to create subtle and precise changes in the genome of the recipient cell. Thus, the present invention provides a means for manipulating and modulating gene expression and regulation.

In particular, the invention provides a mean for manipulating and modulating gene expression and protein structure through the replacement of a gene sequence with a "non-selectable" "desired gene sequence." A gene sequence is non-selectable if its presence or expression in a recipient cell provides no survival advantage to the cell under the culturing conditions employed. Thus, by definition, one cannot select for cells which have received a "non-selectable" gene sequence. In contrast, a "dominant" gene sequence is one which can under certain circumstances provide a survival advantage to a recipient cell. The neomycin resistance conferred by the nptII gene is a survival advantage to a cell cultured in the presence of neomycin or G418. The nptII gene is thus a dominant, rather than a non-selectable gene sequence.

In particular, the invention permits the replacement of a gene sequence which is present in the recipient cell with an "analog" sequence. A sequence is said to be an analog of another sequence if the two sequences are substantially similar in sequence, but have minor changes in sequence corresponding to single base substitutions, deletions, or insertions with respect to one another, or if they possess "minor" multiple base alterations. Such alterations are intended to exclude insertions of dominant selectable marker genes.

When the desired gene sequence, flanked by regions of homology with the recipient cell, is introduced into the recipient cell as a linear double stranded molecule, whose termini correspond to the regions of homology, a single recombination event with the cell's genome will occur in approximately 5% of the transfected cells. Such a single recombinational event will lead to the integration of the entire linear molecule into the genome of the recipient cell.

The structure generated by the integration of the linear molecule will undergo a subsequent, second recombinational event (approximately $10^{-5}$–$10^{-7}$ per cell generation). This second recombinational event will result in the elimination of all DNA except for the flanking regions of homology, and the desired DNA sequence from the integrated structure.

Thus, the consequence of the second recombinational event is to replace the DNA sequence which is normally present between the flanking regions of homology in the cell's genome, with the desired DNA sequence, and to eliminate the instability of gene replacement.

The DNA molecule containing the desired gene sequence may be introduced into the pluripotent cell by any method which will permit the introduced molecule to undergo recombination at its regions of homology. Some methods, such as direct microinjection, or calcium phosphate transformation, may cause the introduced molecule to form concatemers upon integration. These concatemers may resolve themselves to form non-concatemeric integration structures. Since the presence of concatemers is not desired, methods which produce them are not preferred. In a preferred embodiment, the DNA is introduced by electroporation (Toneguzzo, F. et al., *Nucleic Acids Res.* 16:5515–5532 (1988); Quillet, A. et al., *J. Immunol.* 141:17–20 (1988); Machy, P. et al., *Proc. Natl. Acad, Sci.* (U.S.A.) 85:8027–8031 (1988); all of which references are incorporated herein by reference).

After permitting the introduction of the DNA molecule(s), the cells are cultured under conventional conditions, as are known in the art.

In order to facilitate the recovery of those cells which have received the DNA molecule containing the desired gene sequence, it is preferable to introduce the DNA containing the desired gene sequence in combination with a second gene sequence which would contain a detectable marker gene sequence. For the purposes of the present invention, any gene sequence whose presence in a cell permits one to recognize and clonally isolate the cell may be employed as a detectable marker gene sequence.

In one embodiment, the presence of the detectable marker sequence in a recipient cell is recognized by hybridization, by detection of radiolabelled nucleotides, or by other assays of detection which do not require the expression of the detectable marker sequence. Preferably, such sequences are detected using PCR (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194), which references are incorporated herein by reference).

PCR achieves the amplification of a specific nucleic acid sequence using two oligonucleotide primers complementary to regions of the sequence to be amplified. Extension products incorporating the primers then become templates for subsequent replication steps. PCR provides a method for selectively increasing the concentration of a nucleic acid molecule having a particular sequence even when that molecule has not been previously purified and is present only in a single copy in a particular sample. The method can be used to amplify either single or double stranded DNA.

Most preferably, however, the detectable marker gene sequence will be expressed in the recipient cell, and will result in a selectable phenotype. Examples of such preferred detectable gene sequences include the hprt gene (Littlefield, J. W., Science 145:709–710 (1964), herein incorporated by reference), a xanthine-guanine phosphoribosyltransferase (gpt) gene, or an adenosine phosphoribosyltransferase (aprt) gene (Sambrook et al., In: Molecular Cloning A Laboratory Manual, 2nd. Ed., Cold Spring Harbor Laboratory Press, N.Y. (1989), herein incorporated by reference), a tk gene (i.e. thymidine kinase gene) and especially the tk gene of herpes simplex virus (Giphart-Gassler, M. et al., Mutat. Res. 214:223–232 (1989) herein incorporated by reference), the nptII gene (Thomas, K. R. et al., Cell 51:503–512 (1987); Mansour, S. L. et al., Nature 336:348–352 (1988), both references herein incorporated by reference), or other genes which confer resistance to amino acid or nucleoside analogues, or antibiotics, etc. Examples of such genes include gene sequences which encode enzymes such as dihydrofolate reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase) (Sambrook et al., In: Molecular Cloning A Laboratory Manual, 2nd. Ed., Cold Spring Harbor Laboratory Press, N.Y. (1989), herein incorporated by reference).

Cells that do not contain an active thymidine kinase (TK) enzyme, a hypoxanthine-phophoribosyltransferase (HPRT) enzyme, a xanthine-guanine phosphoribosyltransferase (XGPRT) enzyme, or an adenosine phosphoribosyltransferase (APRT) enzyme, are unable to grow in medium containing hypoxanthine, aminopterin, and/or mycophenolic acid (and preferably adenine, xanthine, and/or thymidine), and thymidine, but are able to grow in medium containing nucleoside analogs such as 5-bromodeoxyuridine, 6-thioguanine, 8-azapurine, etc. (Littlefield, J. W., Science 145:709–710 (1964); Sambrook et al., In: Molecular Cloning A Laboratory Manual, 2nd. Ed., Cold Spring Harbor Laboratory Press, N.Y. (1989)).

Conversely, cells that do contain such active enzymes are able to grow in such medium, but are unable to grow in medium containing nucleoside analogs such as 5-bromodeoxyuridine, 6-thioguanine, 8-azapurine, etc. (Sambrook et al., In: Molecular Cloning A Laboratory Manual, 2nd. Ed., Cold Spring Harbor Laboratory Press, N.Y. (1989)).

Cells expressing active thymidine kinase are able to grow in media containing HATG, but are unable to grow in media containing nucleoside analogues such as 5-azacytidine (Giphart-Gassler, M. et al., Mutat. Res. 214:223–232 (1989)). Cells containing an active HSV-tk gene are incapable of growing in the presence of gangcylovir or similar agents.

The detectable marker gene may be any gene which can complement for a recognizable cellular deficiency. Thus, for example, the gene for HPRT could be used as the detectable marker gene sequence when employing cells lacking HPRT activity. Thus, this gene is an example of a gene whose expression product may be used to select mutant cells, or to "negatively select" for cells which express this gene product.

The nptII gene (Southern, P. J., et al., J. Molec. Appl. Genet. 1:327–341 (1982); Smithies, O. et al., Nature 317:230–234 (1985), which references are incorporated herein by reference) is the most preferred detectable marker gene sequence. Constructs which contain both an nptII gene and either a tk gene or an hprt gene are especially preferred.

A. Use of a Single DNA Molecule Containing Both the Detectable Marker Sequence and the Desired Gene Sequence In a first preferred embodiment, the detectable marker gene sequence, flanked by the regions of homology, is provided to the recipient cells on the same DNA molecule which contains the desired gene sequence. As discussed previously, it is preferred that this DNA molecule be a linear molecule.

After selection for cells which have incorporated the desired DNA molecule (for example by selection for G418 resistant cells when the detectable marker gene sequence is an expressible nptII gene sequence), the cells are cultured, and the presence of the introduced DNA molecule is confirmed as described above. Approximately $10^7$ cells are cultured and screened for cells which have undergone the second recombinational event (discussed above) resulting in the replacement of a native sequence (i.e. a gene sequence which is normally and naturally present in the recipient cell) with the desired gene sequence.

Any of a variety of methods may be used to identify cells which have undergone the second recombinational event. Direct screening of clones, use of PCR, use of hybridization probes, etc., may all be employed for this purpose. In a preferred embodiment, the DNA molecule will, in addition to the desired gene sequence, the flanking regions of homology and the detectable marker gene sequence, contain an additional gene sequence which will permit the selection or recognition of cells which have undergone the second recombinational event. This additional gene sequence will be excised from the cell's genome as a direct consequence of the second recombinational event. Thus, gene sequences which are suitable for this purpose include any gene sequence whose loss from a cell can be detected or selected for. Examples of such "negative selection" gene sequences include the hprt gene, and the tk gene (especially the tk gene of herpes simplex virus).

In the first preferred embodiment, the frequency of the second recombinational event is approximately $10^{-5}$. However, the use of a "negative selection" gene sequence permits one to identify such recombinant cells at a frequency of approximately 100%.

Figure 2A:
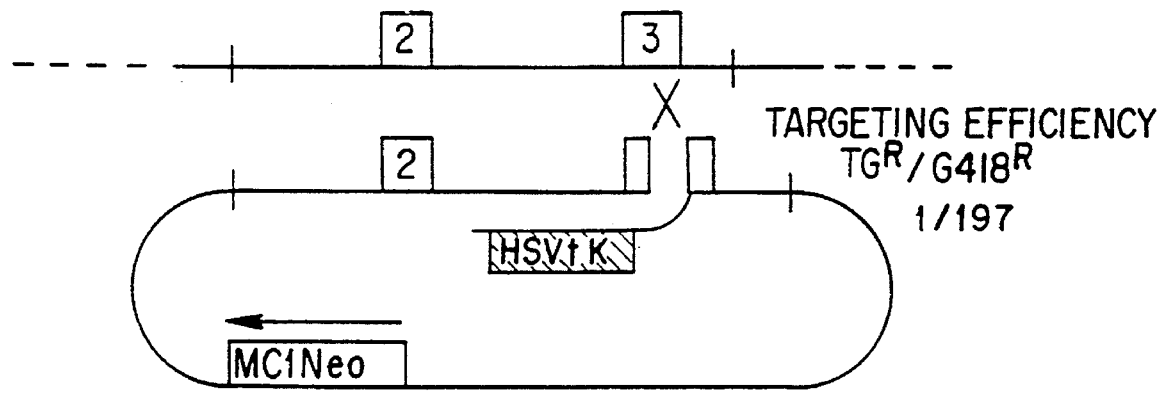
FIG. 2A shows a construct with a 2 kb region of heterology.
Figure 2B:
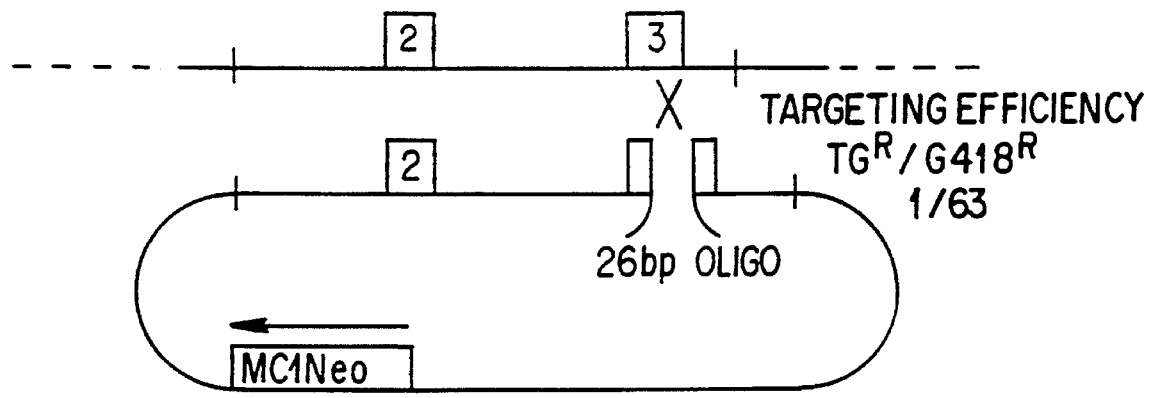
FIG. 2B shows a construct with a 26 base long region of heterology which has been linearized at the center of the region of heterology.

As illustrated in FIG. 2, the DNA molecule may have a region of heterology located at the proposed insertion site. Insertion of such a vector permits one to select for recombinants which have recombined at the insertion site (and not at other potential sites). If recombination occurs at the desired insertion site, it will lead to the loss of the sequence of heterology located at the proposed insertion site of the DNA molecule (HSVtk, for example, in FIG. 2A). Insertions which result from other recombinational events will retain the sequence of heterology. Thus, by employing a region of heterology which encodes an assayable gene product, or which can be used as a "negative selectable" marker, one can readily determine that the locus of insertion of the recipient cell contains the precise sequence desired. As indicated in FIG. 2A), the efficiency of such a vector is approximately $1/197$.

The region of heterology which may be introduced at the insertion site of the DNA molecule may be either short (for example, 26 base pairs, FIG. 2B) or of substantial size (for example, 2 kb, FIG. 2A). The site of linearization may be 5', 3' or within the region of heterology When the site of linearization is within the region of heterology, the efficiency of gene targeting is 1/63.

Figure 2C:
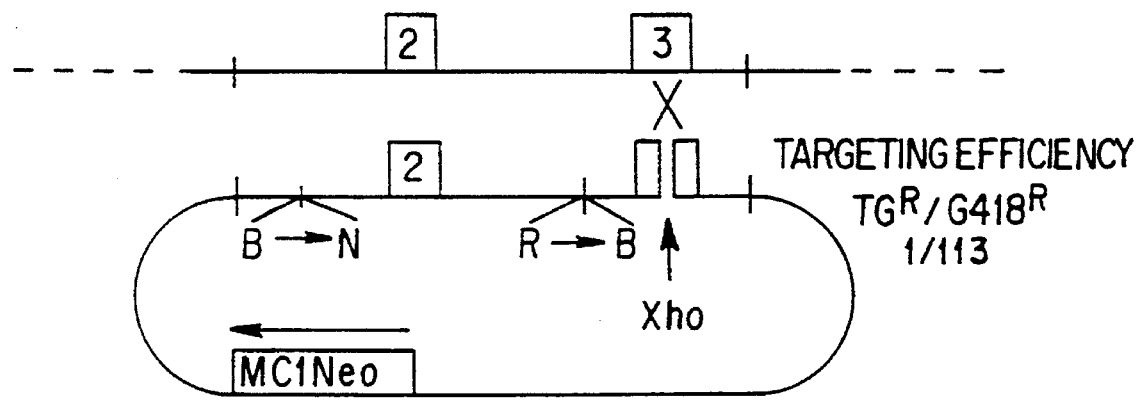
FIG. 2C shows a construct with a region of heterology located internal to the region of homology at which recombination is desired.

As shown in FIG. 2C, the region of heterology may be located at a site internal to the region of homology where the desired recombination shall occur. Such a construct can be used when one desires to introduce a subtle mutation into a locus of the cellular gene at a site other than that of the site of desired recombination.

B. Use of a Different DNA Molecules to Provide the Detectable Marker Sequence and the Desired Gene Sequence In a second preferred embodiment, the detectable marker gene sequence, flanked by the regions of homology, will be provided to the recipient cell on a different DNA molecule from that which contains the desired gene sequence. It is preferred that these molecules be linear molecules.

When provided on separate DNA molecules, the detectable marker gene sequence and the desired gene sequence will most preferably be provided to the recipient cell by coelectroporation, or by other equivalent techniques.

After selection of such recipients (preferably through the use of a detectable marker sequence which expresses the nptII gene and thus confers cellular resistance to the antibiotic G418), the cells are grown up and screened to confirm the insertion event (preferably using PCR).

In the absence of any selection, only one cell in $10^7$ would be expected to have the predicted recombinant structures. If, however, one selects for recipient cells which contain and express a detectable marker sequence (such as the nptII gene), it is possible to obtain a $10^3$ to $10^5$ fold enrichment for cells which have taken up both DNA molecules. Typically, such enrichment enables one to identify the desired recipient cell (in which the introduced DNA has integrated into the cell's genome) by screening only 800–1,500 cells. Such screening is preferably done using PCR, or other equivalent methods. Using such negative selection techniques, one may manipulate the vector copy number.

The two introduced DNA molecules will generally not have integrated into the same site in the genome of the recipient cell. Thus, in some cases, the desired gene sequence will have integrated in a manner so as to replace the native cellular gene sequence between the flanking regions of homology. The locus of integration of the detectable marker gene is unimportant for the purposes of the present invention, provided it is not genetically linked to the same locus as the desired gene sequence. If desired, however, it is possible to incorporate a gene sequence capable of negative selection along with the DNA containing the detectable marker sequence. Thus, one can ultimately select for cells which have lost the introduced selectable marker gene sequence DNA.

C. Use of Direct Selection to Identify Homologous Recombination Events

Figure 13B:
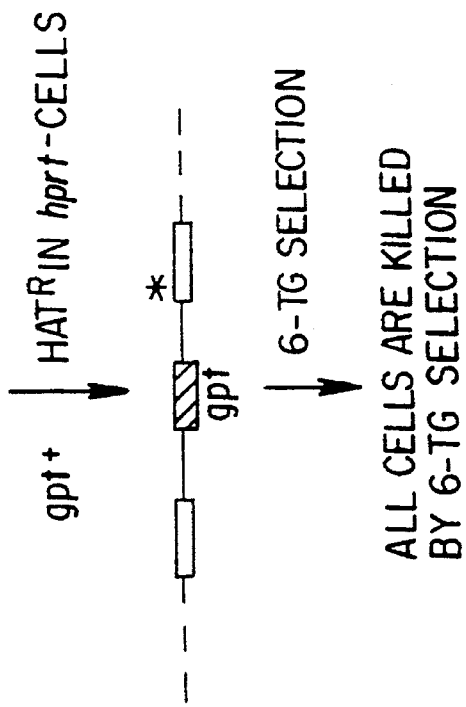
FIG. 13 illustrates a comparison between targeted and random recombinational events. In a random recombinational event, although concatemers can excise duplications, one copy of the vector must remain in the genome. In contrast, in a targeted recombinational event, all sequences, except the desired sequence is excised from the genome.
Figure 13A:
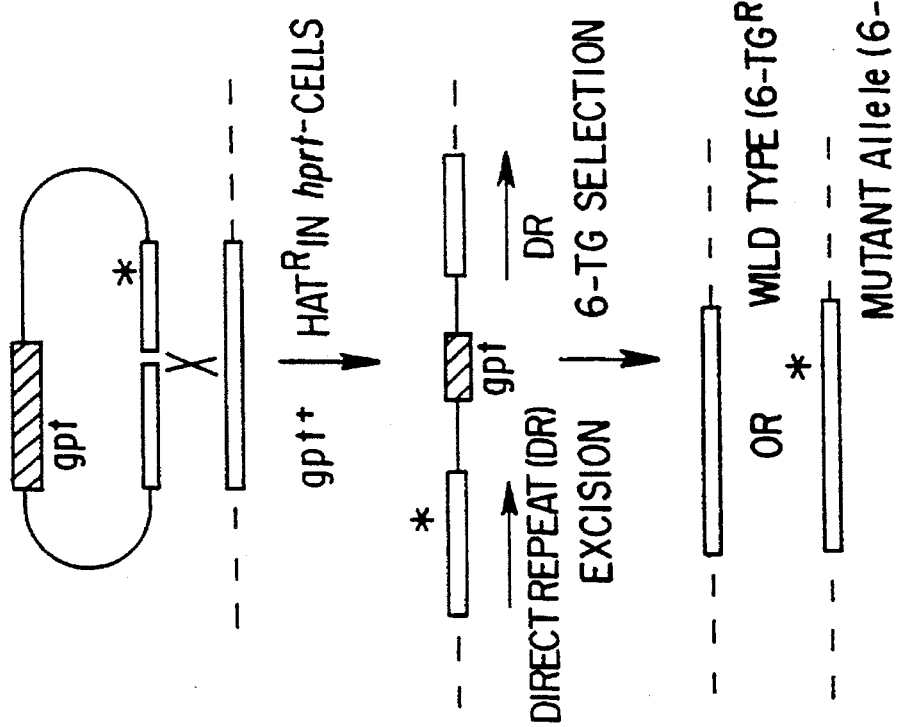

Although all of the above-described preferred embodiments enable the isolation of cells in which one of a cell's alleles has been mutated to contain a desired gene sequence, each embodiment requires the screening of a significant number of candidate cells in order to identify the desired recombinant cell. It is, however, possible to directly select for the desired recombinant cell by employing a variation of the above embodiments. This embodiment of the invention is illustrated in FIG. 13. In the methods illustrated in FIG. 13, if the sequence located below the asterisk is a neo gene, then only the mutant revertants will be selected if 6-thioguanine and G418 selection is applied to select for the excision events.

The method for direct selection of the desired cells relies upon the phenotypic difference in targeted and non-targeted cells and the use of a single gene which can be used for both positive and negative selection.

Typically, in any homologous recombination experiment performed with an insertion vector, three populations of cells will be created. The first class of cells will be those which have failed to receive the desired DNA molecule. This class will comprise virtually all of the candidate cells isolated on completion of the experiment. The second class of cells will be those cells in which the desired gene sequence has been incorporated at a random insertion site (i.e. a site other than in the gene desired to be mutated). Approximately one cell in $10^3$–$10^4$ total cells will be in this class. The third class of cells will be those cells in which the desired gene sequence has been incorporated by homologous recombination into a site in the desired gene. Approximately one cell in $10^5$–$10^6$ total cells will be in this class.

In the above-described embodiments, the cells of the first class (non-transfected cells) can be eliminated by positive selection, thus necessitating the screening of only about 1,000 cells in order to identify the desired recombinant cell. In the present embodiment, cells of the third class (homologous recombinants) may be selected from the cells of the second class (random insertions) if a phenotypic difference exists between the cells of the two classes.

Since random integration sites are likely to be concatemeric with few single copy clones (depending upon the DNA concentration with which the cells were transfected), such integration events are inherently unstable. Thus, such concatemeric constructs will typically undergo intrachromosomal recombination. Such recombination will always leave one intact copy of the vector in the genome. Thus, all random insertion events may be negatively selected from the population if a negatively selectable marker is included on the vector.

In contrast, cells in which the desired gene sequence has been incorporated into the desired gene by homologous recombination will revert with a relatively high frequency (approximately 1 in $10^4$–$10^5$ per cell division (depending upon the size of the duplicated structure) to produce a mutated desired gene that does not contain vector sequences. Therefore, even if the vector contained a negatively selectable gene sequence, such cells will survive negative selection, and can be recovered. The majority of homologous recombinant cells do not undergo reversion, and will be eliminated by the negative selection. Thus, the sum of the selections will result in the isolation of the desired recombinants.

The method comprises incubating a "precursor cell" (i.e. a cell which is to be changed by application of the method into the "desired" recombinant cell) under non-selective culture conditions, or under a first set of selective culture conditions. A culturing condition (i.e. medium, temperature, etc.) is said to be "non-selective" if it is capable of promoting the growth (or sustaining the viability) of a precursor cell, a desired cell, and an intermediate cell type (i.e. a cell obtained during the progression of a precursor cell into a desired cell). A culturing condition is said to be "selective" if it is capable of promoting the growth (or sustaining the viability) of only certain cells (i.e. those having a particular genotype and which therefore contain a particular gene product in either an active or an inactive form).

Preferred selective culturing conditions thus depend upon the genotype of the precursor cell. As stated above, cells that do not contain an active thymidine kinase (TK) enzyme, a hypoxanthine-phophoribosyltransferase (HPRT) enzyme, a xanthine-guanine phosphoribosyltransferase (XGPRT) enzyme, or an adenosine phosphoribosyltransferase (APRT) enzyme, are unable to grow in medium containing hypoxanthine, aminopterin, and/or mycophenolic acid (and preferably adenine, xanthine, and/or thymidine), and thymidine, but are able to grow in medium containing nucleoside analogs such as 5-bromodeoxyuridine, 6-thioguanine, 8-azapurine, etc. Conversely, cells that do contain such active enzymes are able to grow in such medium, but are unable to grow in medium containing nucleoside analogs such as 5-bromodeoxyuridine, 6-thioguanine, 8-azapurine, etc.

Such incubation is conducted in the presence of a DNA molecule containing a desired non-selectable gene sequence. Preferably, the DNA molecule additionally contains two regions of homology which flank this desired gene sequence, and which are sufficient to permit the desired gene sequence to undergo homologous recombination with a predetermined gene sequence of the genome of the precursor cell. The DNA molecule additionally contains a selectable gene sequence whose presence or expression in the cell can be selected for by culturing the cell under a first set of selective culture conditions, and whose presence or expression in the cell can be selected against by culturing the cell under a second set of selective culture conditions.

Examples of preferred selectable gene sequences include gene sequences which encode an active thymidine kinase (TK) enzyme, a hypoxanthine-phophoribosyltransferase (HPRT) enzyme, a xanthine-guanine phosphoribosyltransferase (XGPRT) enzyme, or an adenosine phosphoribosyltransferase (APRT) enzyme. Such gene sequences can be used for both positive and negative selection.

Additional gene sequences which can be used as selectable gene sequences include those which encode enzymes such as dihydrofolate reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase). Methods for producing cells deficient in expressing these enzymes are described by Sambrook et al, (In: *Molecular Cloning A Laboratory Manual*, 2nd. Ed., Cold Spring Harbor Laboratory Press, N.Y. (1989), herein incorporated by reference). Such gene sequences can be used only for positive selection.

The incubation is performed under conditions sufficient to permit the DNA molecule to be introduced into the precursor cell. Such introduced DNA molecules are able to then undergo homologous recombination with the predetermined gene sequence of the genome of the precursor cell to thereby produce the desired cell wherein the desired non-selectable gene sequence has been inserted into the predetermined gene sequence.

Such a desired cell can be recovered by culturing the cell under the first set of selective culture conditions, by then permitting the cell to undergo intrachromosomal recombination under non-selective culture conditions, and by then incubating the cell under the second set of selective culture conditions.

Thus, in one preferred embodiment, the precursor cell lacks an active hypoxanthine-phophoribosyltransferase (HPRT) enzyme, a xanthine-guanine phosphoribosyltransferase (XGPRT) enzyme, or an adenosine phosphoribosyltransferase (APRT) enzyme, and the selectable gene sequence expresses an active HPRT, XGPRT or APRT enzyme. In the first set of selectable culture conditions, medium containing hypoxanthine, aminopterin and/or mycophenolic acid (and preferably adenine, xanthine, and/or thymidine) is employed. In the second set of selectable culturing conditions, medium containing a nucleoside analog such as 5-bromodeoxyuridine, 6-thioguanine, 8-azapurine, etc., is employed.

In a second preferred embodiment, the precursor cell lacks an active TK enzyme, and the selectable gene sequence expresses an active TK enzyme. In the first set of selectable culture conditions, medium containing hypoxanthine, aminopterin, and thymidine is employed. In the second set of selectable culturing conditions, medium containing a thymidine analog such as FIAU (Borrelli, *Proc. Natl. Acad. Sci.* (U.S.A.) 85:7572 (1988), or gangcyclovir, etc. is employed (if an HSV tk gene is used), or 5-bromodeoxyuridine, etc. (if a cellular tk gene is employed).

A preferred negative selectable marker is the hprt gene (cells expressing an active HPRT enzyme are unable to grow in the presence of certain nucleoside analogues such as 6-thioguanine, etc.). When using 6-thioguanine as a negative selection agent, a density of $10^4$ cells / $cm^2$ is preferably used since the efficiency of 6-thioguanine selection is cell density dependent. A typical experiment with $10^7$ transfected cells would yield approximately 10 revertant cells after successive selection. The relative yield of revertant clones can be substantially increased by using "Poly A Selection" for the first round of selection. "Poly A Selection" is discussed in detail in Example 6 below.

IV. The Production of Chimeric and Transgenic Animals

The chimeric or transgenic animals of the present invention are prepared by introducing one or more DNA molecules into a precursor pluripotent cell, most preferably an ES cell, or equivalent (Robertson, E. J., In: *Current Communications in Molecular Biology*, Capecchi, M. R. (ed.), Cold Spring Harbor Press, Cold Spring Harbor, N.Y. (1989), pp. 39–44, which reference is incorporated herein by reference). The term "precursor" is intended to denote only that the pluripotent cell is a precursor to the desired ("transfected") pluripotent cell which is prepared in accordance with the teachings of the present invention. The pluripotent (precursor or transfected) cell may be cultured in vivo, in a manner known in the art (Evans, M. J. et al., *Nature* 292:154–156 (1981)) to form a chimeric or transgenic animal.

Any ES cell may be used in accordance with the present invention. It is, however, preferred to use primary isolates of ES cells. Such isolates may be obtained directly from embryos such as the CCE cell line disclosed by Robertson, E. J., In: Current Communications in Molecular Biology, Capecchi, M. R. (ed.), Cold Spring Harbor Press, Cold Spring Harbor, N.Y. (1989), pp. 39–44), or from the clonal isolation of ES cells from the CCE cell line (Schwartzberg, P. A. et al., *Science* 246:799–803 (1989), which reference is incorporated herein by reference). Such clonal isolation may be accomplished according to the method of E. J. Robertson (In: *Teratocarcinomas and Embryonic Stem Cells: A Practical Approach*, (E. J. Robertson, Ed.), IRL Press, Oxford, 1987) which reference and method are incorporated herein by reference. The purpose of such clonal propagation is to obtain ES cells which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage. An example of ES cell lines which have been clonally derived from embryos are the ES cell lines, AB1 (hprt$^+$) or AB2.1 (hprt$^-$).

The ES cells are preferably cultured on stomal cells (such as STO cells (especially SNC4 STO cells) and/or primary embryonic fibroblast cells) as described by E. J. Robertson (In: *Teratocarcinomas and Embryonic Stem Cells: A Practical Approach*, (E. J. Robertson, Ed.), IRL Press, Oxford, 1987, pp 71–112), which reference is incorporated herein by reference. The stomal (and/or fibroblast) cells serve to eliminate the clonal overgrowth of abnormal ES cells. Most preferably, the cells are cultured in the presence of leukocyte inhibitory factor ("lif") (Gough, N. M. et al., *Reprod. Fertil. Dev.* 1:281–288 (1989); Yamamori, Y. et al., *Science* 246:1412–1416 (1989), both of which references are incorporated herein by reference). Since the gene encoding lif has been cloned (Gough, N. M. et al., *Reprod. Fertil. Dev.* 1:281–288 (1989)), it is especially preferred to transform stomal cells with this gene, by means known in the art, and to then culture the ES cells on transformed stomal cells that secrete lif into the culture medium.

ES cell lines may be derived or isolated from any species (for example, chicken, etc.), although cells derived or isolated from mammals such as rodents (i.e. mouse, rat, hamster, etc.), rabbits, sheep, goats, fish, pigs, cattle, primates and humans are preferred.

V. The Production of Chimeric and Transgenic Plants

The chimeric or transgenic plants of the invention are produced through the regeneration of a plant cell which has received a DNA molecule through the use of the methods disclosed herein.

All plants from which protoplasts can be isolated and cultured to give whole regenerated plants can be transformed by the present invention so that whole plants are recovered which contain the introduced gene sequence. Some suitable plants include, for example, species from the genera *Fragaria, Lotus, Medicago, Onobrychis, Trifolium, Trigonella, Vigna, Citrus, Linum, Geranium, Manicot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Zea, Triticum, Sorghum, Ipomoea, Passiflora, Cyclamen, Malus, Prunus, Rosa, Rubus, Populus, Santalum, Allium, Lilium, Narcissus, Ananas, Arachis, Phaseolus, Pisum* and *Datura*.

There is an increasing body of evidence that practically all plants can be regenerated from cultured cells or tissues, including but not limited to all major cereal crop species, sugarcane, sugar beet, cotton, fruit and other trees, legumes and vegetables.

Plant regeneration from cultural protoplasts is described in Evans et al., "Protoplast Isolation and culture," in *Handbook of Plant Cell Culture* 1:124–176 (MacMillan Publishing Co., New York, 1983); M. R. Davey, "Recent Developments in the Culture and Regeneration of Plant Protoplasts," *Protoplasts*, 1983—Lecture Proceedings, pp. 19–29 (Birkhauser, Basel, 1983); P. J. Dale, "Protoplast Culture and Plant Regeneration of Cereals and Other Recalcitrant Crops," in *Protoplasts* 1983—Lecture Proceedings, pp. 31–41 (Birkhauser, Basel, 1983); and H. Binding, "Regeneration of Plants," in *Plant Protoplasts*, pp. 21–37 (CRC Press, Boca Raton, 1985).

Regeneration varies from species to species of plants, but generally a suspension of transformed protoplasts containing the introduced gene sequence is formed. Embryo formation can then be induced from the protoplast suspensions, to the stage of ripening and germination as natural embryos. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

The mature plants, grown from the transformed plant cells, are selfed to produce an inbred plant. The inbred plant produces seed containing the introduced gene sequence. These seeds can be grown to produce plants that express this desired gene sequence.

Parts obtained from the regenerated plant, such as flowers, seeds, leaves, branches, fruit, and the like are covered by the invention. Progeny and variants, and mutants of the regenerated plants are also included within the scope of this invention.

As used herein, variant describes phenotypic changes that are stable and heritable, including heritable variation that is sexually transmitted to progeny of plants.

VI. GENE EXPRESSION

In one embodiment, the DNA molecule(s) which are to be introduced into the recipient cells in accordance with the methods of the present invention will be incorporated into a plasmid or viral vector (or a derivative thereof) capable of autonomous replication in a host cell.

Preferred prokaryotic vectors include plasmids such as those capable of replication in *E. coli* such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli*, Academic Press, N.Y. (1982), pp. 307–329). Suitable *Streptomyces* plasmids include pIJ101 (Kendall, K. J., et al., *J. Bacteriol.* 169:4177–4183 (1987)), and *Streptomyces* bacteriophages such as φC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Examples of suitable yeast vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982)).

Examples of vectors which may be used to replicate the DNA molecules in a mammalian host include animal viruses such as bovine papilloma virus, polyoma virus, adenovirus, or SV40 virus.

VII. Uses of the Present Invention

The methods of the present invention permit the introduction of a desired gene sequence into an animal or plant cell.

In a first embodiment, the methods of the present invention may be used to introduce DNA into germ line cells of animals in order to produce chimeric or transgenic animals which contain a desired gene sequence. The animals which may be produced through application of the described method include chicken, non-human mammals (especially, rodents (i.e. mouse, rat, hamster, etc.), rabbits, sheep, goats, fish, pigs, cattle and non-human primates).

As stated above, the desired gene sequence may be of any length, and have any nucleotide sequence. In particular, it is possible to design the sequence of the desired gene sequence in order to create single, or multiple base alterations, insertions or deletions in any preselected gene of a cell.

If such changes are within a translated region of a native gene sequence, then a new protein variant of a native protein can be obtained. Such a procedure can, for example be used to produce animals which produce improved (i.e. more stable, more active, etc.) enzymes, binding proteins, receptors, receptor ligands, etc.

The methods of the present invention may be used to produce cells in which a natural gene has been replaced with a heterologous gene. A gene is said to be heterologous to a transgenic cell if it is derivable from a species other than that of the transgenic cell.

Figure 3:
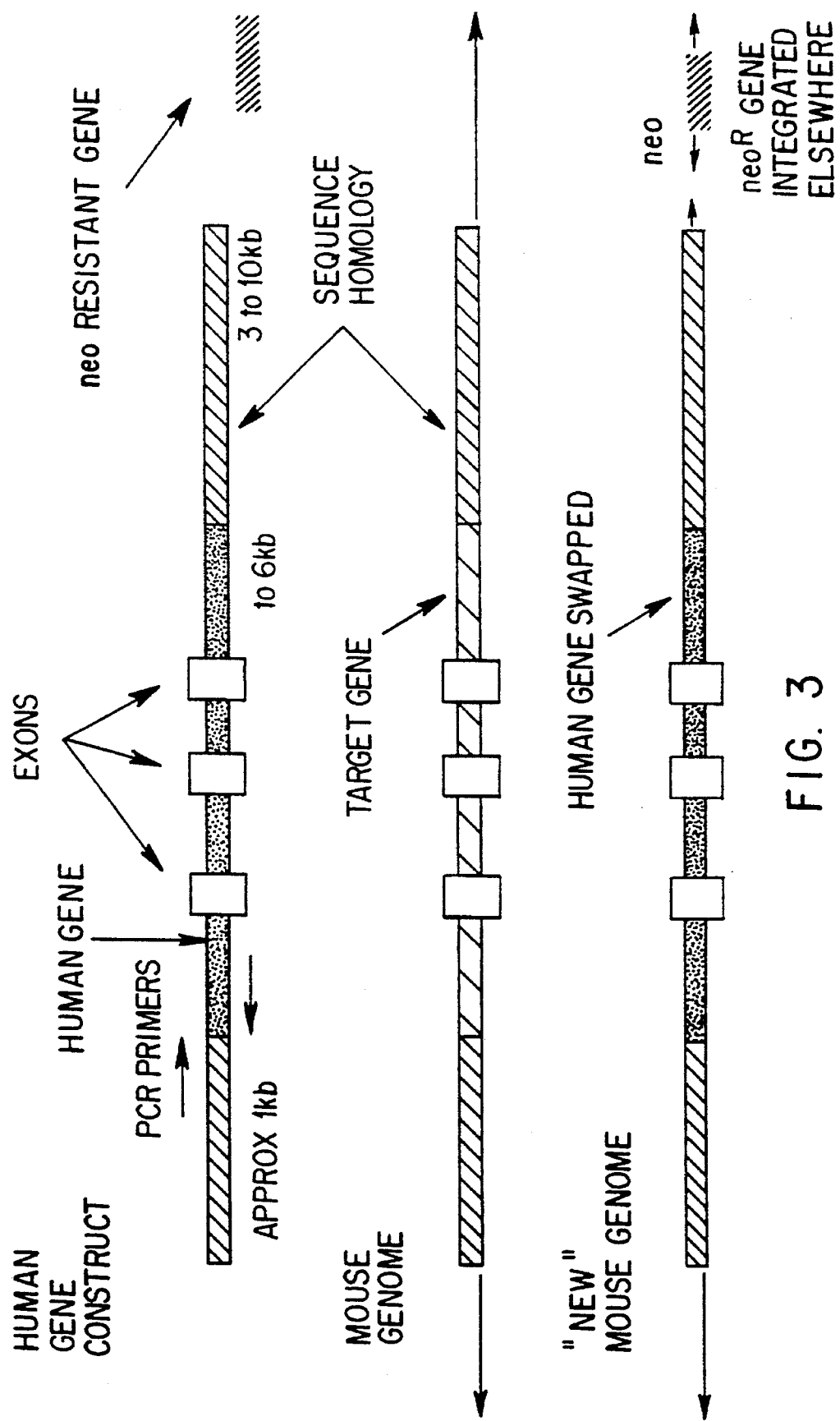
FIG. 3 is a diagrammatical representation of the mechanism through which a "humanized" gene may be introduced into a chromosomal gene sequence in a one step method.

In one embodiment, this replacement may be accomplished in a single step (FIG. 3). To accomplish such replacement, a DNA molecule containing a desired gene sequence and a region of homology is introduced into a recipient cell. A selectable marker gene is also introduced into the cell, and used to select for cells which have underwent recombination. The method results in the replacement of the normal sequences adjacent to the region of homology with the heterologous sequences of the desired DNA sequence.

Figure 4A:
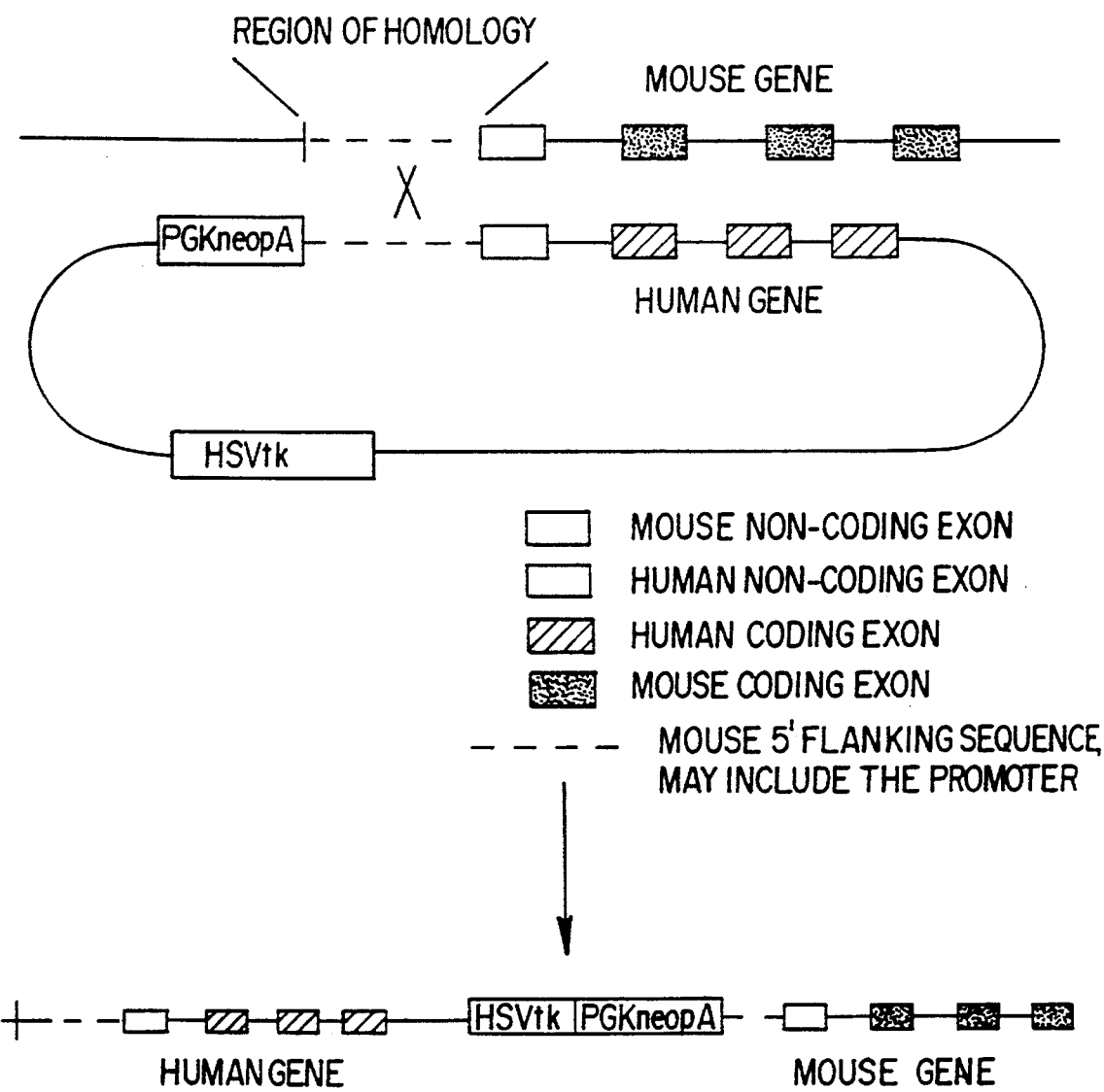
FIG. 4A shows the first step of the process.

In a second embodiment, this replacement may be accomplished in a two steps (FIG. 4). As in the embodiment described above, a cell is provided with a DNA molecule containing a desired gene sequence and a region of homology. The DNA molecule also contains a selectable marker gene used to select for cells which have undergone a recombinational event that has resulted in the insertion of the introduced DNA molecule into their chromosomes at the site of homology. The structure of such an insertion site is depicted in FIG. 4A.

Significantly, in this embodiment, the introduced DNA molecule will also contain a "negative selectable" marker gene which can be used to select for cells which undergo a second recombinational event that results in the loss of the inserted DNA.

Figure 4B:
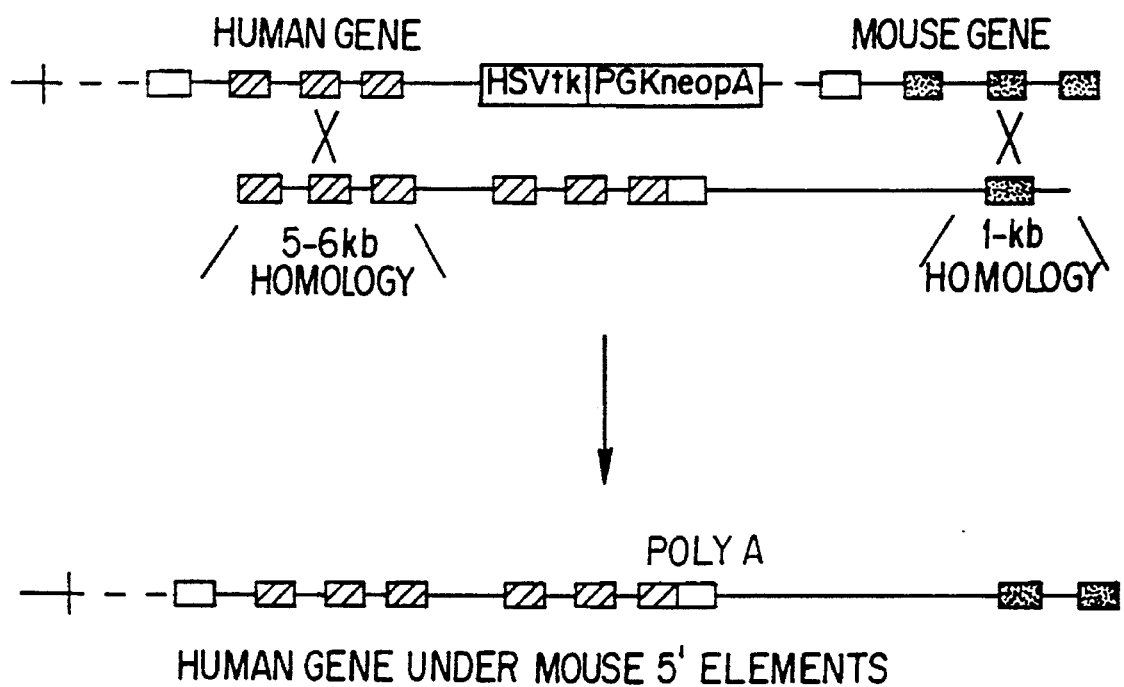
FIG. 4B shows the second step of the process. The repair recombination event may be configured to remove all of the mouse coding exons if desired.

As shown in FIG. 4B, a second DNA molecule is employed to complete the gene replacement. This second DNA molecule need not contain any selectable marker gene. Upon receipt of the second DNA molecule, a second recombinational event occurs which exchanges the "second" DNA molecule for the integrated "first" DNA molecule (including the desired DNA sequence, the selectable marker sequence, and the "negative selectable" marker sequence contained on that molecule). This aspect of the invention is illustrated in FIG. 4B.

Figure 5A:
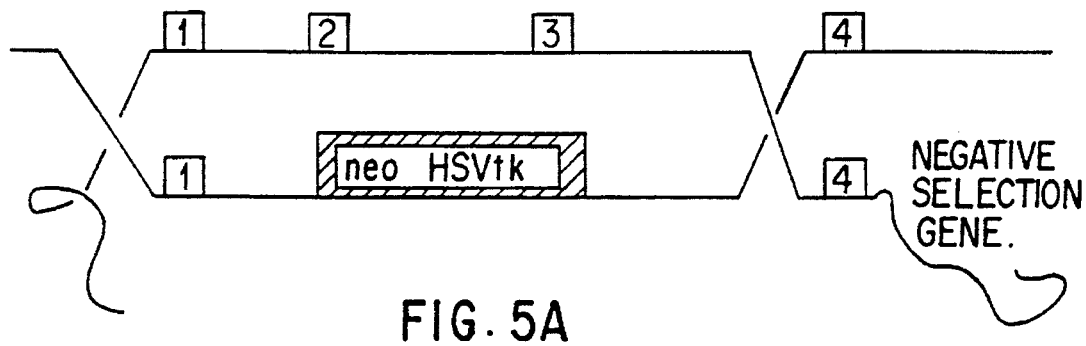
FIG. 5 is a diagramatical representation of the use of a positive selection/ negative selection "cassette" to introduce subtle mutations into a chromosome.
Figure 5B:
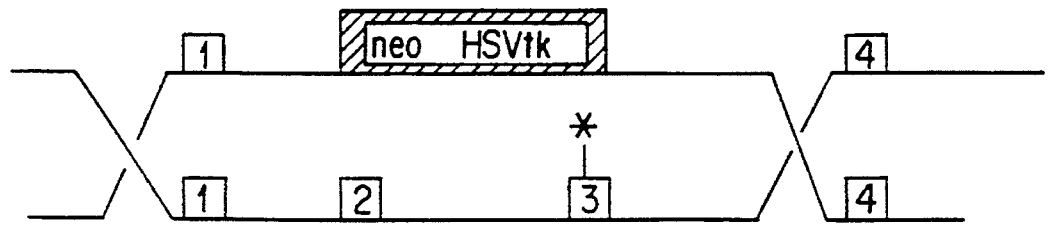
Figure 5B:
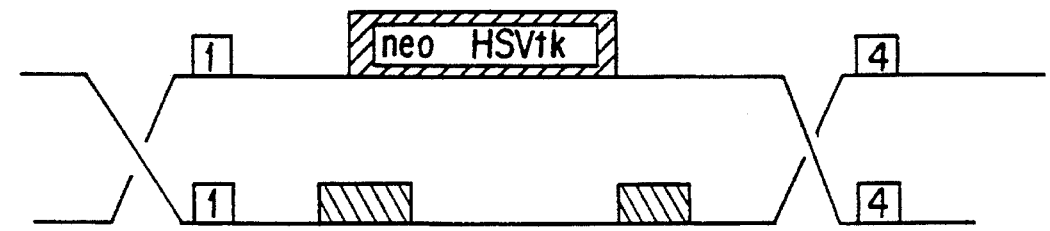

In another embodiment of the invention, subtle mutations may be introduced into a desired locus using a "cassette" construct containing both a positive selection marker (such as the nptII gene or the gpt gene) and a negative selection marker (such as the tk gene). In this embodiment, one first uses the positive selection capacity of the construct to introduce the two selection markers into a desired locus. One then introduces the desired subtle mutations (substitutions, insertions, deletions, etc.) by providing a cell with a DNA molecule that contains the desired mutation. By selecting for the loss of the "cassette" (using the negative selection marker), one can select for recombinational events which result in the replacement of the "cassette" sequence with the DNA sequence containing the desired mutation. This embodiment of the invention is illustrated in FIG. 5.

The methods of the present invention may also be used to replace contiguous regions of a chromosome with any desired gene sequence. Thus, the present invention is not limited in the size of the DNA regions which may be altered or replaced. This aspect of the present invention is illustrated in FIG. 6, as a series of 5 steps (FIGS. 6A–6E). The method is applicable to any gene sequence. It is especially useful in producing cells which contain heterologous immunoglobulins (such as the heavy chain locus of an immunoglobulin).

Figure 6A:
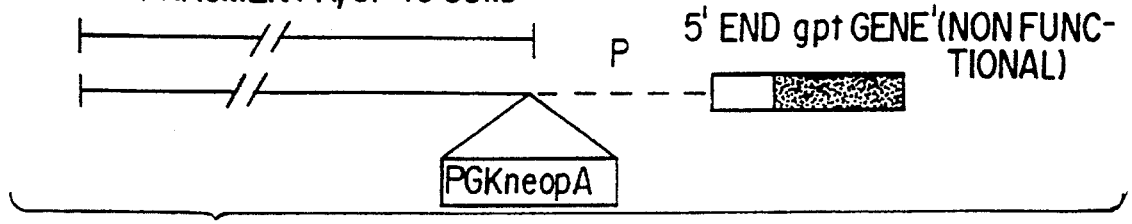
FIG. 6 is a diagrammatical representation of a multistep method (FIGS. 6A–6E) for introducing small or large desired gene sequences into a contiguous region of a cell's genome. The figure illustrates a vector capable of facilitating the sequential addition of overlapping clones to construct a large locus. Every step is selectable. Subsequent additions may be made by returning to steps 4 and 5 as many times as required, selecting for insertion in HAT medium, and for repair in media supplemented with 6 thioguanine. This procedure may also be accomplished at the other end of the locus if required.

The first step in replacing a large region of a chromosome with a desired sequence involves setting up an initial target. In this step, a recipient cell is provided with a DNA molecule which contains a "first fragment" of the total desired replacement sequence (FIG. 6A). This "first fragment" of the desired replacement sequence contains a selectable marker sequence (most preferably the nptII gene) at its end.

The DNA molecule also contains a "dual selection" gene sequence which encodes a non-functional fragment of a gene sequence for which both a positive and a negative selection exists. An example of such a gene is the gpt gene when used in the context of an hprt⁻ cell. Cells which express a functional gtp gene can be selected for by their ability to grow in HAT medium; Cells which lack a functional gpt gene can be selected for by their ability to grow in the presence of 6-thioguanine.

Homologous recombination results in the insertion of the DNA molecule into the cell's genome at the region of homology (FIG. 6A). Importantly, since this step results in the creation of a cell whose genome contains the selectable marker gene, it is possible to select for the desired recombinational event.

Figure 6B:
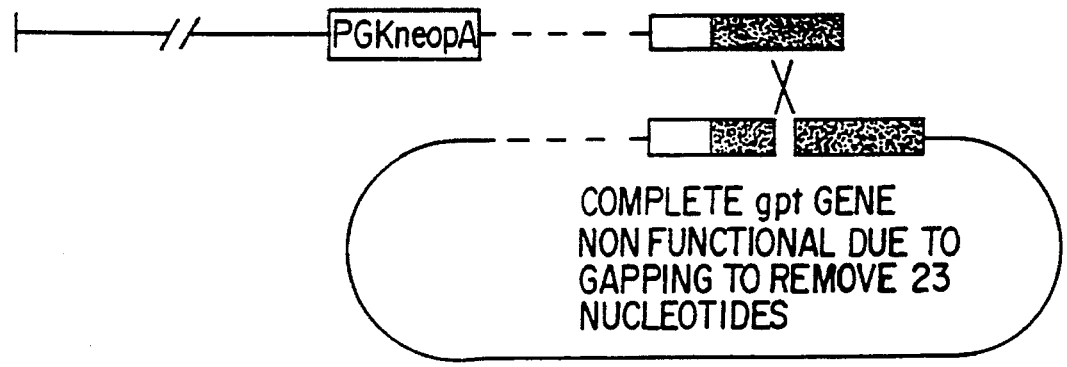
Figure 6B:

In the second step of the method, a second DNA molecule is provided to the cell. This second DNA molecule contains a "second fragment" of the desired replacement sequence as well as a sequence of the dual selection gene that, due to an internal deletion, is incapable of encoding a functional gene product. Homologous recombination results in the insertion of the second DNA molecule into the cell's genome in a manner so as to create a functional dual selection gene (FIG. 6B). Recombination also results in the integration of a non-functional fragment of the dual selection gene. Importantly, since this step results in the creation of a cell whose genome contains a functional dual selection gene, it is possible to select for the desired recombinational event.

Figure 6C:
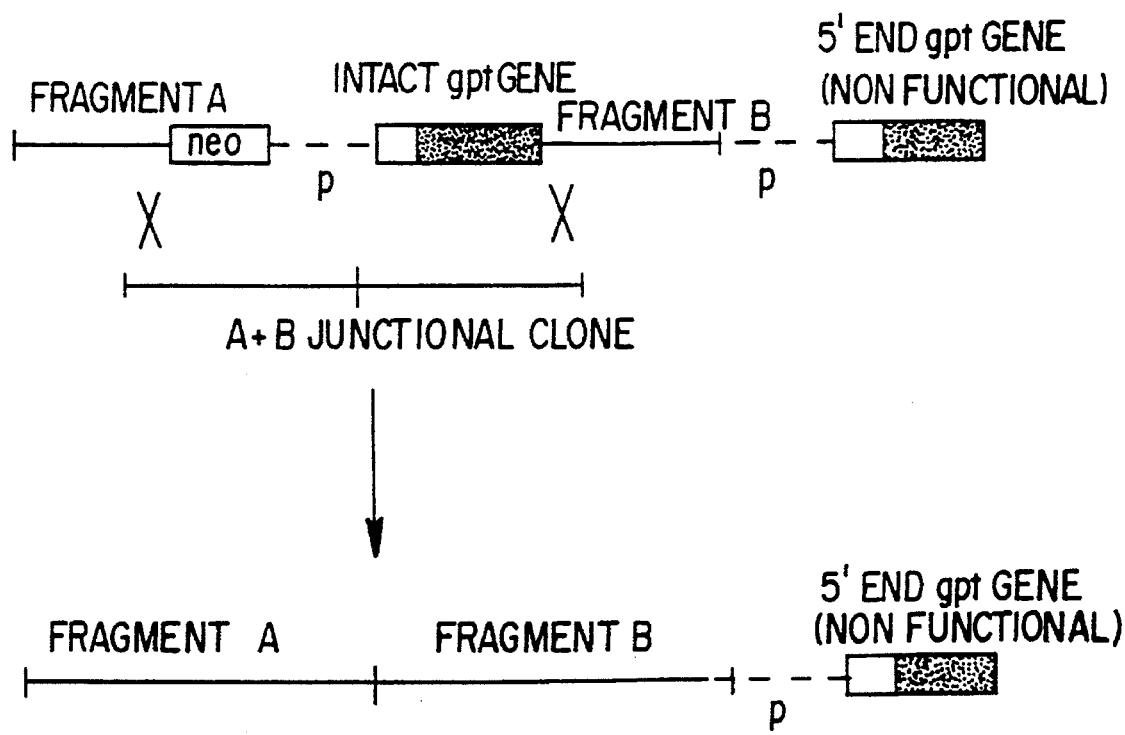

In the third step of the method, a third DNA molecule is provided to the cell. This third DNA molecule contains both the "first" and "second" fragments of the desired replacement sequence. Homologous recombination results in the insertion of the third DNA molecule into the cell's genome in a manner so as to delete the functional dual selection gene. The non-functional fragment of the dual selection gene (formed in step 2) is not affected by the recombination, and is retained (FIG. 6C). Importantly, since this step results in the creation of a cell whose genome lacks the dual selection gene, it is possible to select for the desired recombinational event.

Figure 6D:
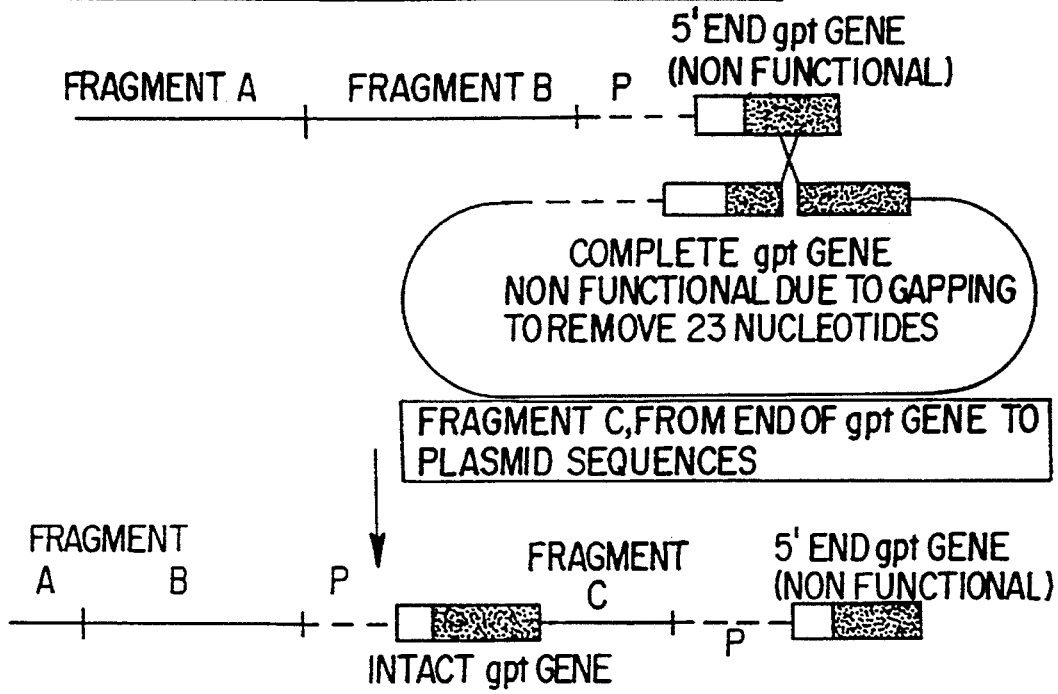
Figure 6E:
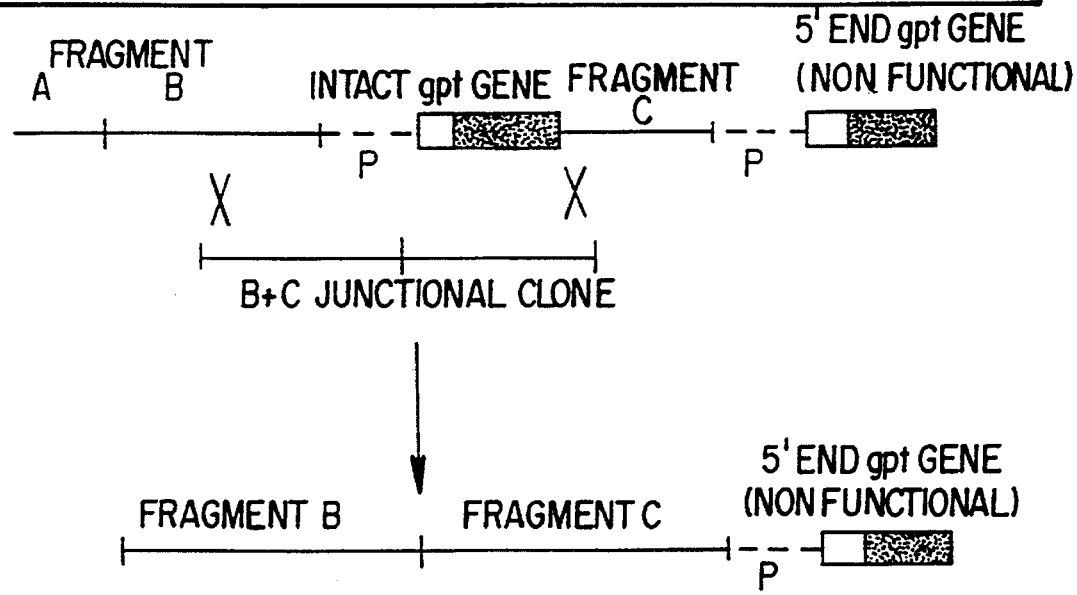

In the fourth step of the method, a fourth DNA molecule is provided to the cell. This fourth DNA molecule contains a "third fragment" of the desired replacement sequence as well as a sequence of the dual selection gene that, as in step 2, is incapable of encoding a functional gene product due to an internal deletion. Homologous recombination results in the insertion of the fourth DNA molecule into the cell's genome in a manner so as to create a functional dual selection gene (FIG. 6D). Recombination also results in the integration of a non-functional fragment of the dual selection gene. Importantly, since this step results in the creation of a cell whose genome contains a functional dual selection gene, it is possible to select for the desired recombinational event.

In the fifth step of the method, a fifth DNA molecule is provided to the cell. This fifth DNA molecule contains both the "second" and "third" fragments of the desired replacement sequence. Homologous recombination results in the insertion of the fifth DNA molecule into the cell's genome in a manner so as to delete the functional dual selection gene. The non-functional fragment of the dual selection gene (formed in step 4) is not affected by the recombination, and is retained (FIG. 6C). Importantly, since this step results in the creation of a cell whose genome lacks the dual selection gene, it is possible to select for the desired recombinational event.

As will be appreciated, the net effect of the above-described steps is to produce a cell whose genome has been engineered to contain a "first," "second," and "third" "fragment" of a particular desired gene in a contiguous manner. The steps may be repeated as desired in order to introduce additional "fragments" into the cell's genome. In this manner, cells can be constructed which contain heterologous genes, chromosome fragments, or chromosomes, that could not be introduced using a single vector. As indicated above, each step of the method can be selected for.

In particular, this aspect of the present invention may be used to produce "humanized" antibodies (i.e. non-human antibodies which are non-immunogenic in a human) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041–1043 (1988); Liu, A. Y. et al., Proc. Natl. Acad. Sci. USA 84:3439–3443 (1987); Liu, A. Y. et al., J. Immunol. 139:3521–3526 (1987); Sun, L. K. et. al., Proc. Natl. Acad. Sci. USA 84:214–218 (1987); Nishimura, Y. et al., Canc. Res.47:999–1005 (1987); Wood, C. R. et al., Nature 314:446–449 (1985)); Shaw et al., J. Natl. Cancer Inst. 80:1553–1559 (1988).

The method may also be used to produce animals having superior resistance to disease, animals which constitute or produce improved food sources, animals which provide fibers, hides, etc. having more desirable characteristics. The method may also be used to produce new animal models for human genetic diseases. For example, the method may be used to "humanize" the CD4 analog of an animal, and thus provide an animal model for AIDS. Such animal models can be used for drug testing, and thus hasten the development of new therapies for genetic diseases.

In addition, the present invention permits the formation of cells and of transgenic animals which contain mutations in medically or clinically significant heterologous genes. A gene is said to be medically or clinically significant if it expresses an isotype of a protein associated with a human or animal disease or condition. Examples of such genes include the genes which encode: topoisomerase p180, 5-αreductase, ACAT, 5-lipoxygenase, the insulin receptor, the interleukin-2 receptor, the epidermal growth factor receptor, the seratonin receptor, the dopamine receptor, the GABA receptor, the $V_2$ vasopressin receptors, G proteins (signal transduction), phospholipase C proteins, and insulin. A transgenic mouse produced by microinjection which expresses human insulin was reported by Selden, R. F. et al. (European Patent Publication No. 247,494, which reference is incorporated herein by reference).

The transgenic cells and animals discussed above can be used to study human gene regulation. For example, transgenic animals which express a human isotype of topoisomerase p180, 5-α reductase, ACAT,5-lipoxygenase, or hormone or cytokine receptors would have ultility in in vivo drug screening. The expression of topoisomerase p180 is associated with resistance to chemotherapeutics. Thus, agents which interfere with this enzyme could be used to enhance the effectiveness of chemotherapy. An animal, especially a rat, capable of expressing a human isotype of 5-α reductase (especially in the prostate gland) would be highly desirable. ACAT is a key enzyme in lipid metabolism; an animal model for its regulation would be extremely valuable. Animals that express 5-lipoxygenase could be of interest to many research programs, particularly to screen isotype selective inhibitors. An animal which expressed human hormone or cytokine receptor proteins would be valuable in identifying agonists and antagonists of receptor action. Similarly, an aminal that expressed components of the human signal transduction system (i.e. G proteins and phospholipase Cs, etc.) could be used to study the pathophysiologic consequences of disordered function of these proteins.

The present invention can be used to produce cells and animals which express human isotypes of transport proteins (i.e. proteins which facilitate or enable the transport of other molecules or ions across membranes in the gut, blood brain barrier, kidney, etc.). Such cells or animals can then be used to study the role of such proteins in metabolism. In particular, the extent and patterns of conjugation mediated by such isotypes may be studied in order to investigate the pharmacokinetic consequences of specific differences in protein structure or sequence. Glucoronide transferase, glycine conjugation and sulfation, methylases, and glutathione conjugation are examples of enzymes of particular interest in this regard.

The clearance of many compounds is mediated by esterases. Cells or animals which express heterologous isotypes of such esterases may be exploited in investigating such clearance.

Cells or animals which express isotypes of proteins involved in azo or nitro reduction would be desirable for research on the processes of azo or nitro reduction.

Significantly, potential therapeutic agents are frequently found to induce toxic effects in one animal model but not in another animal model. To resolve the potential of such agents, it is often necessary to determine the metabolic patterns in various species, and to then determine the toxicities of the metabolites. The present invention permits one to produce transgenic cells or animals which could facilitate such determinations.

The methods of the present invention may be used to produce alterations in a regulatory region for a native gene sequence. Thus, the invention provides a means for altering the nature or control of transcription or translation of any native gene sequence which is regulated by the regulatory region. For example, it is possible to introduce mutations which remove feedback inhibition, and thus result in increased gene expression. Similarly, it is possible to impair the transcriptional capacity of a sequence in order to decrease gene expression. Such alterations are especially valuable in gene therapy protocols, and in the development of improved animal models of human disease. For example, the capacity to increase insulin gene transcription or translation provides a potential genetic therapy for diabetes. Similarly, the ability to impair the synthesis of beta globin chains provides an animal model for betathalassemia.

The methods of the present invention, quite apart from their uses in veterinary and human medicine, may be used to investigate gene regulation, expression and organization in animals.

Since the methods of the present invention utilize processes of DNA repair and recombination, agents which inhibit or impair the present methods may act by affecting these processes. Since agents which impair DNA repair and recombination have potential antineoplastic utility, the present invention provides a means for identifying novel antineoplastic agents.

The present invention may additionally be used to facilitate both the cloning of gene sequences, and the mapping of chromosomes or chromosomal abnormalities.

Since the desired gene sequence need not be homologous or analogous to any native gene sequence of the recipient cell, the methods of the present invention permit one to produce animals which contain and express foreign gene sequences. If the cell expresses an analogous gene, the desired gene sequence may be expressed in addition to such analogous cellular genes (for example, an animal may express both a "humanized" receptor and an analogous native receptor). Thus, for example, the invention provides a means for producing animals which express important human proteins (such as human interferons, tissue plasminogen activator, hormones (such as insulin and growth hormone), blood factors (such as Factor VIII), etc.).

In a second embodiment, the methods of the invention may be used to introduce DNA into plant cells which can then be manipulated in order to produce chimeric or transgenic plants. The plants which may be produced through application of the disclosed method include all multicellular, higher (i.e. non-fungal) plants. A non-fungal plant is any plant which is not a fungus or yeast.

In a third embodiment, the methods of the invention may be used to introduce DNA into the somatic cells of an animal (particularly mammals including humans) or plant in order to provide a treatment for genetic disease (i.e. "gene therapy"). The principles of gene therapy are disclosed by Oldham, R. K. (In: *Principles of Biotherapy*, Raven Press, N.Y., 1987), and similar texts.

In this third embodiment, the genetic lesion which causes the disease is replaced with a gene sequence encoding a preferred gene product. Examples of such genetic lesions are those responsible for diseases such as cystic fibrosis, phenylketonuria, hemophilia, von Willebrand's Disease, sickle cell anemia, thalassemia, galactosemia, fructose intolerance, diseases of glycogen storage, hypercholesterolemia, juvenile diabetes, hypothyroidism, Alzheimer's Disease, Huntington's Disease, Gout, Lesch-Nyhan Syndrome, etc. (Bondy, P. K. et al., In: *Disorders of Carbohydrate Metabolism*, pp 221–340, Saunders (1974); Coleman, J. et al., *Molecular Mechanisms of Disease*, Yale University Press, (1975)). Disclosures of the methods and uses for gene therapy are provided by Boggs, S. S. (*Int. J. Cell Clon.* 8:80–96 (1990)); Karson, E. M. (*Biol. Reprod.* 42:39–49 (1990)); Ledley, F. D., In: *Biotechnology, A Comprehensive Treatise, volume 7B, Gene Technology*, VCH Publishers, Inc. N.Y., pp 399–458 (1989)); all of which references are incorporated herein by reference.

In a fourth embodiment, the methods of the invention may be used to provide a treatment to protect recipient animals or plants from exposure to viruses, insects or herbicides (in the case of plants), insecticides, toxins, etc. In this embodiment, the introduced gene would provide the recipient with gene sequences capable of mediating either an enhanced or novel expression of an enzyme, or other protein, capable of, for example, degrading an herbicide or toxin. For example, a plant cell may receive a gene sequence capable of mediating an enhanced or novel expression of a chitinase, thus conferring increased resistance to insect parasites.

When providing the desired gene sequence to the cells of an animal, pharmaceutically acceptable carriers (i.e. liposomes, etc.) are preferably employed. Such gene sequences can be formulated according to known methods to prepare pharmaceutically useful compositions, whereby these materials, or their functional derivatives, are combined in admixture with a pharmaceutically acceptable carrier vehicle. Suitable vehicles and their formulation, are described, for example, in Nicolau, C. et al. (*Crit. Rev. Ther. Drug Carrier Syst.* 6:239–271 (1989)), which reference is incorporated herein by reference.

In order to form a pharmaceutically acceptable composition suitable for effective administration, such compositions will contain an effective amount of the desired gene sequence together with a suitable amount of carrier vehicle.

Additional pharmaceutical methods may be employed to control the duration of action. Control release preparations may be achieved through the use of polymers to complex or absorb the desired gene sequence (either with or without any associated carrier). The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate the agent into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions.

In a fifth embodiment, the methods of the present invention may be used to improve the food or fiber characteristics of plants or non-human animals. For example, the methods can be used to increase the overall levels of protein synthesis thereby resulting in faster growing plants or non-human animals, or in the production of plants and non-human animals which have increased food value.

Having now generally described the invention, the same will be more readily understood through reference to the following examples which are provided by way of illustration, and are not intended to be limiting of the present invention, unless specified.

EXAMPLE 1

Electroporation

Electroporation was performed as follows:

DNA Preparation

DNA used for electroporation was purified by CsCl gradient centrifugation. A large-scale digest of this purified DNA was prepared by incubating the DNA with an appropriate restriction enzyme. The large-scale digest was examined for complete digestion by running 500 ng on a minigel. The DNA concentration of the large-scale digest should be no higher than 1 µg/µl.

The large-scale digest was then extracted once with an equal volume of phenol/chloroform and once with an equal volume of chloroform. The DNA was precipitated with 2.4 volumes of ethanol, pelleted by centrifugation, and dried using a Speed-Vac.

The pelleted DNA was then resuspended at the desired concentration (usually 1 µg/µl) in a sterile Tris-EDTA buffer such as 0.1X TE (25 µl of DNA per electroporation). The concentration of the DNA was then measured with a fluorometer.

Preparation of Cells for Electroporation

Embryonic stem cells of the AB1 cell line were cultured to approximately 80% confluence according to the methods of E. J. Robertson (In: *Teratocarcinomas and Embryonic Stem Cells: A pratical Approach*, (E. J. Robertson, Ed.), IRL Press, Oxford, 1987, pp 71–112). Cells were cultured in the presence of stomal cells which expressed lif into the culture medium. Cells were passaged 1:2 the day before electroporation, and fed 4 hours before harvesting.

Cells were harvested by trypsinizing the cells, and by resuspending in media (cells from 2×10 cm plates were combined in a total volume of 10 ml in a 15 ml tube).

The cells were pelleted by centrifugation, and the supernatant was removed by aspiration. The cells were then resuspended in 10 ml of phosphate buffered saline and the total number of cells was determined by counting a 20 µl aliquot. The usual yield is 30×10$^6$ cells per 10 cm plate.

The cells were then pelleted by centrifugation and the supernatant was removed by aspiration. Cells were resuspended at a density of 11×10$^6$ cells/mi. A 20 µl aliquot was counted to confirm this cell density.

Electroporation

Cells, prepared as described above, were incubated in the presence of an appropriate amount of DNA in a 15 ml tube. 25µl of DNA and 0.9 ml of cells were used for each electroporation.

The mixture was allowed to incubate at room temperature for 5 minutes (this step may, however, be omitted).

The cell/DNA mixture was then carefully aliquoted into electroporation cuvettes (0.9 ml per cuvette; the volume is important). The cuvette was placed in the electroporation holder with the foil electrodes in contact with the metal holding clips.

Electroporation was accomplished using a Biorad GenePulser set at 230V, 500 µF (this requires a capacitance extender). The time constant should read between 5.6 and 7.0.

The cuvette was left at room temperature for 5 minutes and then the cells were plated at an appropriate density (up to 2×10$^7$ cells/100 mmplate or 6×10$^6$ cells/60 mmplate). When G418 was used as a selective agent, this cell density should not be exceeded since G418 takes 3–4 days before killing starts and plates will become over-confluent. When G418 selection was to be applied, it is applied 24 hours post-electroporation. G418 concentration must be titrated for every batch.

The plate(s) were re-fed with fresh media+G418 every day for the first 6–7 days (until colonies are visible and most cell debris has been removed). If using FIAU (0.2 µM) selection, this may proceed simultaneously.

The typical yield for RV4.0 (Thomas, K. R. et al., *Cell* 51:503–512 (1987)) is up to 10$^4$ colonies/10$^7$ cells/100 mm plate. Although this yield may be significantly (and unpredictably) different from the yield obtained when other constructs are used, the use of the method always results in the recovery of some colonies of cells which contain the electroporated DNA.

Colonies may be picked as early as 8 days. It is most preferred to pick colonies at around 10–11 days. Colonies may, however, be recovered up to 18–21 days after the electroporation.

EXAMPLE 2

Co-Electroporation of ES Cells

Figure 7:
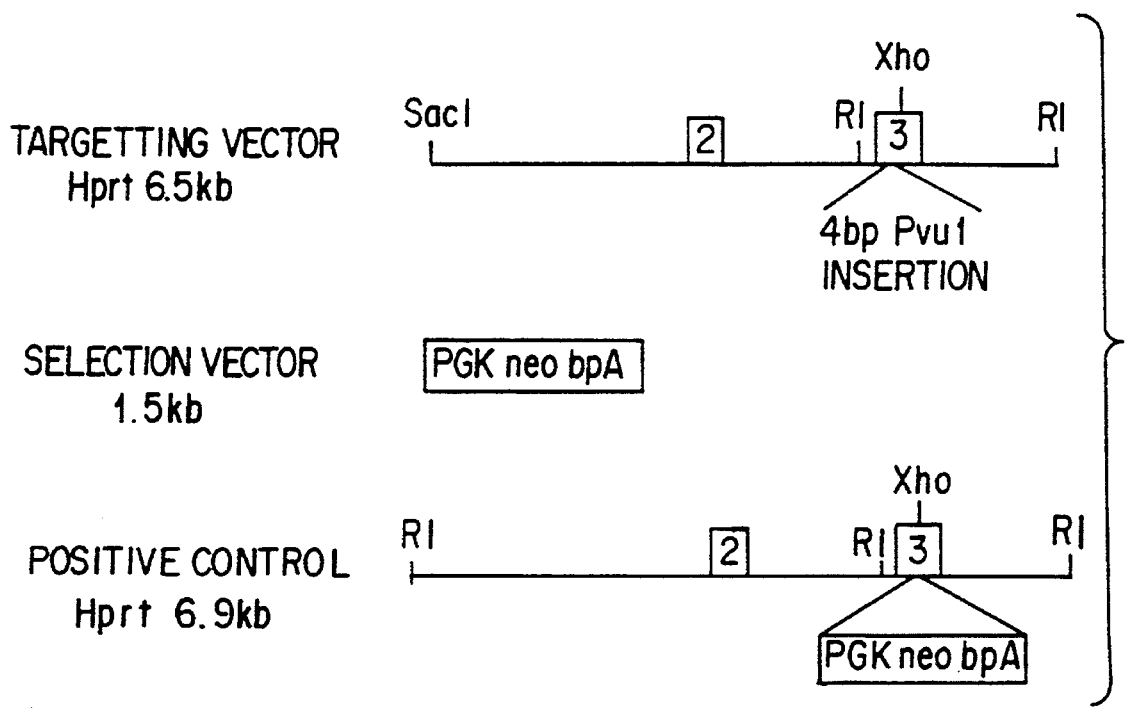
FIG. 7 is a diagrammatical representation of the vectors used in a co-electroporation experiment to mutate the hprt gene.

To illustrate the invention, embryonic stem ("ES") cells were co-electroporated with a 4.5 kb nptII-containing vector (pPGKneobpA) which had been linearized by treatment with XhoI restriction endonuclease, and with the 6.5 kb HPRT vector, AD 8 (linearized with SacI) (FIG. 7). Electroporation (230 V, 500 µF) were done on 0.9 ml aliquot of CCEp24 cells (7.5×10$^6$ cells/ml).

The electroporation reactions were conducted using molar ratios of 1:1, 1:10, and 1:100 (nptII DNA:HPRT DNA). The total amount of DNA provided was either 25, 50, 100, or 200 µg. The vectors used in this experiment are illustrated in FIG. 7. The results of this experiment are shown in Table 1.

TABLE 1

CO-ELECTROPORATION OF nptII AND hprt GENE SEQUENCES
Average of Number of Colonies Formed per 1 × 10⁶ Cells
(μg of DNA (# = Number of trials averaged))

| Ratio of DNA | 200 | | | 100 | | | 50 | | | 25 | | |
|---|---|---|---|---|---|---|---|---|---|---|---|---|
| | G418$^R$ | TG$^R$ | # | G418$^R$ | TG$^R$ | # | G418$^R$ | TG$^R$ | # | G418$^R$ | TG$^R$ | # |
| 1:1 | 233 | 2.7 | 3 | 101 | 1.5 | 3 | 64 | 0 | 3 | 23 | 0 | 5 |
| 1:10 | 46 | 0 | 3 | 16 | 0 | 5 | 8.7 | 0 | 7 | nd | nd | |
| 1:100 | 8 | 0.2 | 5 | 4.3 | 0 | 7 | 1.6 | 0 | 7 | nd | nd | |

This experiment shows that co-electroporation of an hprt gene sequence with an nptII-containing gene sequence in the presence of selection for only the nptII-containing sequence, resulted in recombination of both the nptII and hprt DNA molecules.

The frequencies of recombination are shown in Table 2 below.

TABLE 2

FREQUENCY OF RECOMBINATION

| Expt | Ratio Neo:Hprt | [DNA] μg/ml | G418$^R$/10$^5$ | TG$^R$/10$^7$ | TG$^R$/G418$^R$ |
|---|---|---|---|---|---|
| A | 1:1 | 200 | 23.3 | 2.6 | 1/873 |
| B | 1:1 | 100 | 10.1 | 1.0 | 1/1010 |
| C | 1:100 | 200 | 0.8 | 0.2 | 1/400* |
| Cont | — | 25 | 10.8 | 2.7 | 1/402 |

The reactions were carried out as described above. The reproducibility of the experimental results was examined. The results of this experiment are shown in Table 3.

TABLE 3

EFFECT OF MODIFIED CO-ELECTROPORATION
PROTOCOL ON RECOMBINATION FREQUENCY

| Molar ratios Neo: | DNA per zap (μg) | # of zap | G418$^R$/ HPRT- colonies (total) | HPRT- G418R | HPRT-G418$^R$ (per cell transfected) | |
|---|---|---|---|---|---|---|
| | | | | | (×10$^{-9}$) | (×10$^{-6}$) |
| 1:1 | 200 | 8 | 16,150/32 | 1/504 | 400 | 202 |
| | 100 | 3 | 3,030/3 | 1/1,010 | 100 | 105 |
| | 50 | 3 | 1,920/0 | | 67 | |
| | 25 | 5 | 1,150/0 | | 24 | |
| 1:10 | 200 | 16 | 608/7 | 1/868 | 43 | 47 |
| | 100 | 5 | 800/0 | | 17 | |
| | 50 | 7 | 609/0 | | 9 | |
| 1:100 | 200 | 5 | 400/1 | 1/400 | 8 | |
| | 100 | 7 | 300/0 | | 4.5 | |
| | 50 | 7 | 112/0 | | 1.7 | |

EXAMPLE 3

Homologous Recombination

In order to investigate the chromosomal structure which is produced by the recombination of the vectors of the above-described vectors into the chromosomes of recipient cells, the following experiments were conducted.

For this purpose, a vector was used which contained a 6.5 kb region of homology with the cellular hprt locus. The vector also contained the nptII gene, as a selectable maker.

The vector was linearized with XhoI and provided to ES cells by electroporation, as described above. Cells which became resistant to G418 were selected and their DNA was analyzed to determine if it contained restriction fragments that were consistent with the predicted integration structure.

Figure 8:
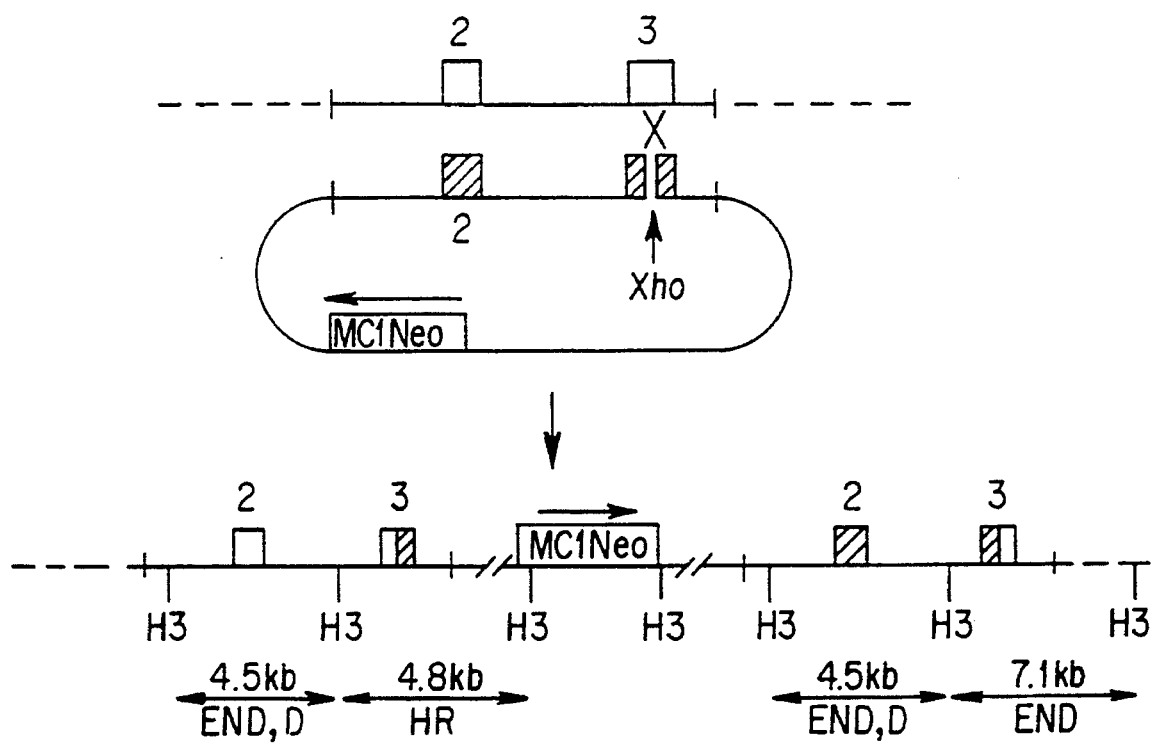
FIG. 8 illustrates the predicted structure of the hprt gene following homologous recombination of the IV6.8 vector. HR is the predicted size fragment indicative of the homologous recombination event. End, D is the endogenous fragment, duplicated by the recombination event. End is the predicted flanking fragment detected by the partial cDNA probe used in these experiments.

The vector used, and the predicted integration structure are illustrated in FIG. 8. Gel electrophoresis of restriction digests of cellular DNA confirmed that the G418 resistant cells contained the hDrt structure shown in FIG. 8. This finding confirmed that the vector had integrated into the chromosome of the cell by homologous recombination at the hprt locus.

EXAMPLE 4

Reversion of Recombinants

Figure 9:
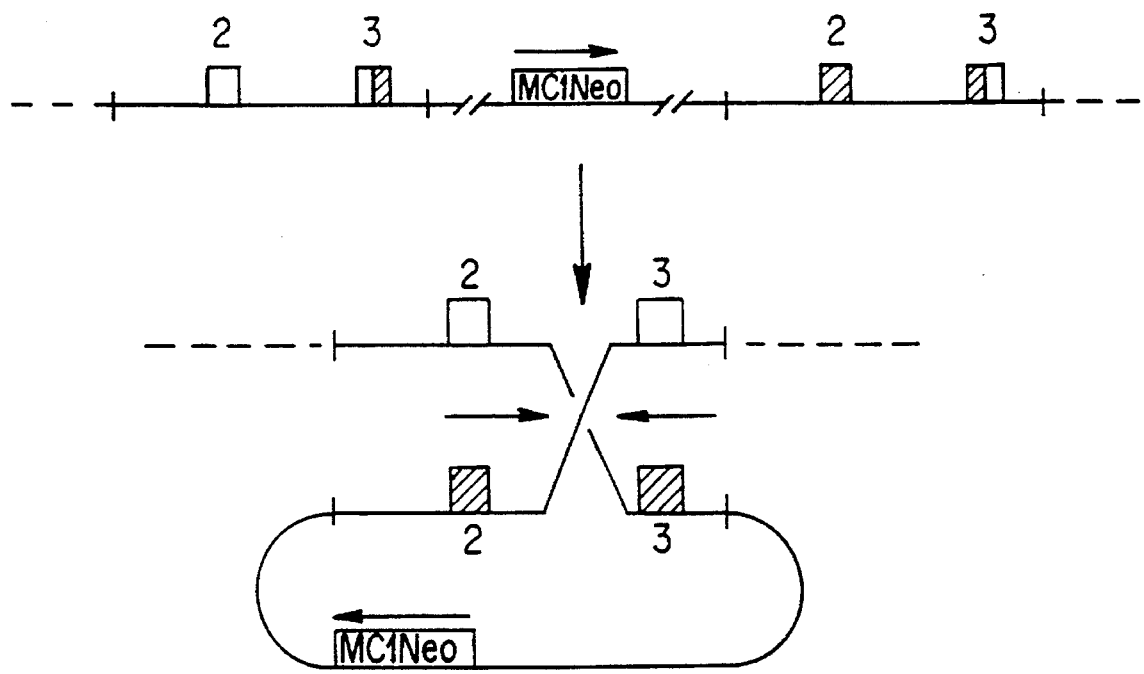
FIG. 9 shows the reversion of homologous recombinants generated with insertion vectors.

The effect of the size of the region of homology carried by the vector on the reversion frequency of recombinants was determined. Recombinants containing a vector having 6.8 kb of homology with the hprt locus were prepared as described in Example 3. Using the same method, recombinants were also prepared which contained a similar vector having only 1.3 kb of homology with the hprt locus. The structures of the insertion site of the 6.8 kb vector is illustrated in FIG. 8. The reversion frequency of the two constructs is shown in Table 4. The structure obtained from the reversion of the insertion is shown in FIG. 9.

TABLE 4

REVERSION FREQUENCY

| Duplication | # Clones | # Revertible | Frequency × 10$^{-5}$ |
|---|---|---|---|
| 6.8 kb | 19 | 19 | 3.3 to 0.2 |
| 1.3 kb | 2 | 2 | 1.2 to 0.3 |

EXAMPLE 5

Targeting Frequency of Insertion and Replacement Vectors

A series of different vectors were used to investigate the targeting frequency achieved through the use of the methods of the invention. These vectors contained 6.8 kb of homology with the murine hprt gene and had regions of heterology either at the linearization site or internally (FIG. 2).

For this purpose, 10$^8$ cells were electroporated into ES cells, prepared as described above, and plated onto 10×90 mm plates. After 24 hours G418 (at 350 μg/ml) was added to the media. After 5 days selection 10$^{-5}$M 6-thioguanine was added to 9 plates, 1 was retained under G418 selection as the transfection control. Selection was continued for an additional 7 days. Colonies were scored at this time and expanded for southern analysis as separate clones. Targeting efficiencies are detailed for each of the vectors (FIG. 2; Table 5).

Southern analysis showed that the majority of the 6-TG$^R$ clones had the predicted integration structure depicted for HindIII digestion in FIG. 8.

Reversion of the hprt clones was done by measuring HAT$^R$. Cells were clonally expanded under 6-TG selection to prevent "jackpot" effects caused by the early recombinational loss of the duplicated element giving rise to a large number of colonies by cell division. When $10^7$ cells were obtained, the cells were reseeded onto 90 mmplates without selection for 48 hours. After 48 hours HAT selection was applied and resistant colonies were scored 10 days later, typically 20 to 200 colonies were observed per $10^7$ cells plated (Table 4). Every clone examined reverted at a similar frequency.

TABLE 5

REPLACEMENT AND INSERTION VECTORS: TARGETING AND FREQUENCY

| Gene | Homology | Vector | Frequency | |
|---|---|---|---|---|
| Hprt | 6.8 kb | RV | 1/300 | 10X |
| Hprt | 6.8 kb | IV | 1/32 | |
| Hprt | 1.3 kb minimum | RV | <1/5000 | 12X |
| Hprt | 6.8 kb | IV | 1/400 | |
| Hprt Ho × 2.6 | 3.2 kb | IV+ | 1/33 | |

RV = Replacement Vector; IV = Insertion Vector

EXAMPLE 6

Selection for Homologous Recombination

It is possible to use "Poly A Selection" in order to enhance the selection of cells which have integrated the introduced DNA by homologous recombination.

If an introduced DNA molecule were to integrate at random into the host chromosome, it would generally not integrate at a site adjacent to a necessary 3' polyadenylation site. Thus, the mRNA produced by the transcription of such randomly inserted constructs would generally lack polyadenylation. This fact can be exploited by using vectors which permit one to select for a recombinational event that results in integration adjacent to the natural polyadenylation site of the introduced gene sequence (i.e. by homologous recombination rather than by random insertion).

Figure 10:
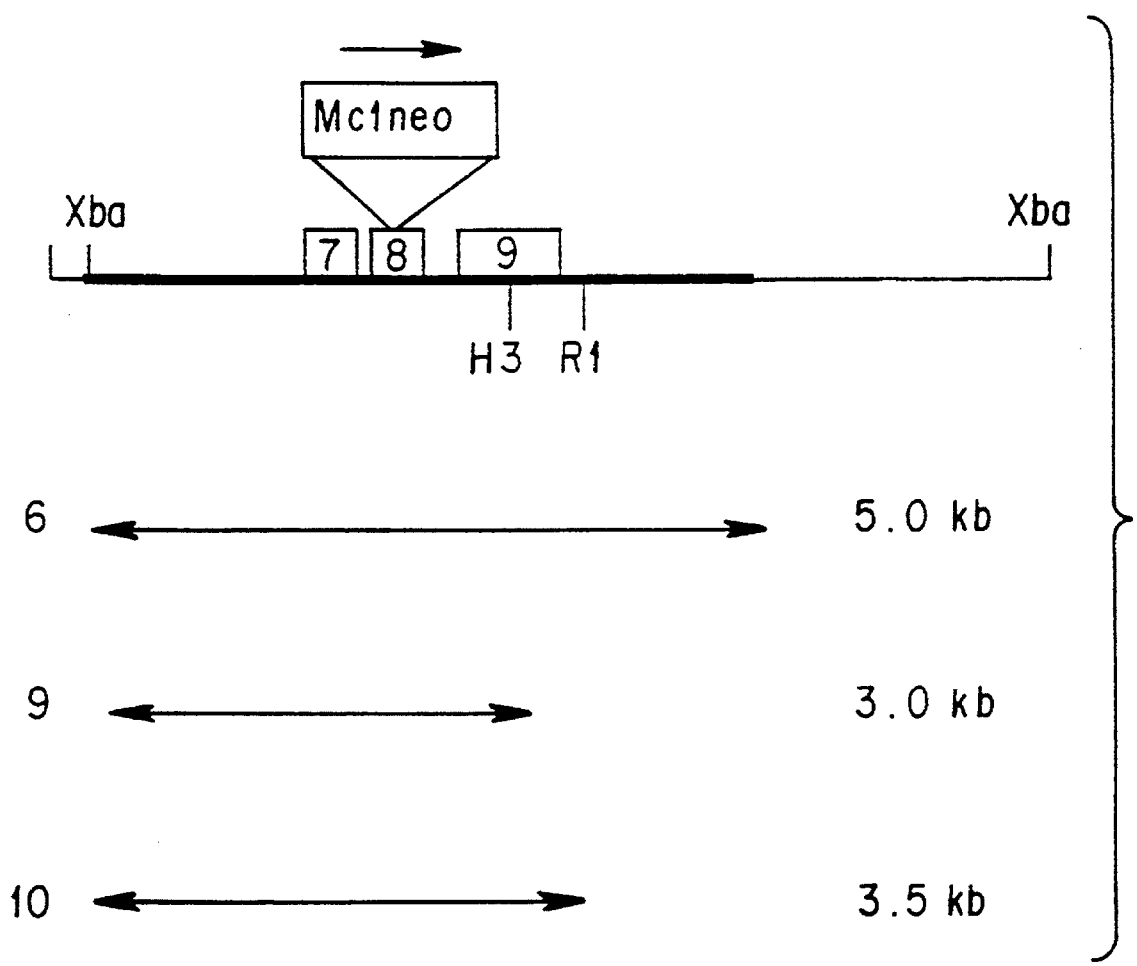
FIG. 10 illustrates the use of Poly A selection as a means for selecting homologous recombination events.

To illustrate this aspect of the invention, three vectors were constructed which contain fragments of the hprt gene (FIG. 10). As shown in FIG. 10, the vectors contain exons 7, 8, and 9 of the hDrt gene. The polyadenylation site is located in exon 9. A HinDIII site is present within exon 9, and an EcoRI site is located after the end of the exon.

The first vector employed contained a 5.0 kb region, and thus contained the polyadenylation site of exon 9 (Vector 6, FIG. 10). As shown in Table 6, the frequency of insertion was high (i.e. frequency of G418 resistant colonies was 24 ×10$^{-5}$), but only 1/941 colonies showed the dual thioguanine resistance and G418 resistance which would characterize a desired recombinant (i.e. a recombinant in which integration had resulted in an intact hprt gene and an intact nptII gene). Thus, some random integration is occurring.

Similarly, when a vector of 3.5 kb was employed (Vector 10) which contained DNA from the XbaI site to the EcoRI site of Vector 6, the frequency of insertion was high (i.e. frequency of G418 resistant colonies was 21×10$^{-5}$), but only 1/770 colonies showed the dual thioguanine resistance and G418 resistance which would characterize a desired recombinant (Table 6). This finding demonstrates that some random integration is occurring.

If, however, a vector is employed which lacks the polyadenylation site of exon 9 (i.e. Vector 9), random integration does not result in expression of a functional nptII transcript. Thus, the frequency of G418 resistant colonies is low (1.4×10$^{-5}$). Since the number of colonies evidencing random integration is suppressed, the overall frequency of recovery of the desired recombinants is enhanced (i.e. an overall efficiency of 1/100 for the dual resistant colonies (Table 6). Thus, the poly A selection results in an approximate increase of overall efficiency of nearly 10 fold. Poly A selection may therefore be advantageously used in situations where one desires to minimize or avoid the screening of colonies to identify random versus homologous recombinants.

TABLE 6

POLY A SELECTION

| VECTOR # | SIZE (kb) | G418$^R$ (×10$^{-5}$) | TG$^R$ (×10$^{-7}$) | TG$^R$/G418$^R$ |
|---|---|---|---|---|
| 6 | 5.0 | 24 | 2.5 | 1/941 |
| 9 | 3.0 | 1.4 | 1.4 | 1/100 |
| 10 | 3.5 | 21 | 2.7 | 1/770 |

EXAMPLE 7

Introduction of Subtle Mutations in the C-SRC Locus

The methods of the present invention were further illustrated by their use to produce cells having precise and subtle mutations in the c-src locus of ES cells. The c-src locus contains several exons, which are designated as "boxed" regions 2 and 3' in FIG. 11. As shown in FIG. 11A, the natural allele of exon 3' does not contain a HindIII site.

The sequence of a portion of exon 3' is shown in FIG. 11C. As shown in FIG. 11C, a 9 bp insertion (SEQ ID NO: SEQ ID NO.3) into this exon will result in the formation of a HinDIII site.

To accomplish this change in the sequence of exon 3', a vector (src 14) was prepared. As shown in FIG. 11B, the src 14 vector is homologous to a region of the c-src locus. The exon 3' sequence of the vector, however, has been altered to contain the 9 base pair insertion needed to create a HindIII site (FIG. 11C).

The src 14 vector was introduced into ES cells by coelectroporation with a second vector (PGKneo) that contained the nptII gene, at a total DNA concentration of 25 μg/ml and a molar ratio of 1:5 (neo vector to targeting vector) in the manner described above.

Cells were cultured in the presence of G418 for 12 days in order to select for recombinant cells in which the nptII gene had integrated. These recombinant cells were then screened, using PCR, for cells which had undergone a recombinational event resulting in the replacement of the natural exon 3' locus with the HinDIII site-containing exon 3' sequence of the src 14 vector.

Southern analysis of the colonies identified by PCR screening using probes B and C (FIG. 11B) demonstrated that the natural exon 3' locus had been altered, as desired, to contain a HinDIII site (SEQ ID No.7 and SEQ ID NO.3). This experiment demonstrated that subtle insertions can be introduced into any cellular gene.

To further illustrate the capacity of the present invention to introduce complex, predetermined mutations into the genome of a recipient cell, exon 3" of the c-src gene of an ES cell was mutated to contain two different substitution mutations.

As shown in FIG. 12A, the natural allele of exon 3" does not contain either an NheI site or an EcoRI site. As shown in FIG. 12C, however, the replacement of the natural sequence ACC TGG TTC of exon 3" with the sequence TAG CTA GCT will result in the formation of an NheI site (SEQ ID NO:4 and SEQ ID NO:6). Similarly, replacement of ACA with GAA in exon 3" will create an EcoRI (SEQ ID NO:4 and SEQ ID NO:6) site (FIG. 12C).

To accomplish these changes in the sequence of exon ", a vector (src 33) was prepared. As shown in FIG. 12B, the src 33 vector is homologous to a region of the c-src locus. The exon 3" sequence of the vector, however, has been altered to contain the substitutions indicated above (FIG. 12C).

The src 33 vector was introduced into ES cells by electroporation, in concert with a second vector that contained the nptII gene, in the manner described above. Cells were cultured in the presence of G418 in order to select for recombinant cells in which the nptII gene had integrated. These recombinant cells were then screened, using PCR, for cells which had undergone a second recombinational event resulting in the replacement of the natural exon 3" locus with the exon 3" sequence of the src 33 vector.

Southern analysis of the colonies identified by PCR screening using probes A and C (FIG. 12C) demonstrated that the natural exon 3" locus had been altered, as desired, to contain both the NheI and the EcoRI sites (SEQ ID NO:4 and SEQ ID NO:6). This experiment demonstrated that subtle substitutions can be introduced into any cellular gene.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

---

What is claimed is:

1. A method for producing a desired mammalian cell which contains a desired gene sequence inserted within a predetermined gene sequence of said cell's genome, which method comprises:

A. introducing into a mammalian cell a DNA molecule comprising:
   i) said desired gene sequence;
   ii) two regions of homology which flank said desired gene sequence wherein said regions are sufficiently homologous with said predetermined gene sequence to undergo homologous recombination with said predetermined gene sequence of said mammalian cell; and
   iii) at least one selectable gene sequence located within said regions of homology which flank said desired gene sequence, wherein the presence of at least on selectable gene sequence in said mammalian cell can be selected for by culturing said mammalian cell under a set of selective culture conditions;

B. permitting said introduced DNA molecule to undergo homologous recombination with said predetermined gene sequence of said mammalian cell to produce an intermediate cell, wherein said desired gene sequence has been inserted into said mammalian cell; and C. recovering said intermediate cell by culturing said intermediate cell under said selective culture conditions;

D. culturing said intermediate cell under conditions such that said intermediate call undergoes intrachromosomal recombination or sister chromated exchange, wherein said at least one selectable gene sequence is deleted from the cell's genome and said desired mammalian cell is produced; and E. recovering said desired mammalian cell.

2. The method of claim 1, wherein said mammalian cells are deficient in HPRT enzyme, wherein said at least one selectable polynucleotide sequence codes for an active HPRT enzyme, and wherein said first set of selective culture conditions comprise conditions in which the presence of an active HPRT enzyme in said mammalian cells is required for growth.

3. The method of claim 1, wherein said mammalian cells are deficient in APRT enzyme, wherein said at least one selectable polynucleotide sequence codes for an active APRT enzyme, and wherein said first set of selective culture conditions comprises conditions in which the presence of an active APRT enzyme in said mammalian cells is required for growth.

4. The method of claim 1, wherein said mammalian cells are deficient in thymidine kinase enzyme, wherein said at least one selectable polynucleotide sequence codes for an active thymidine kinase enzyme, and wherein said first set of selective culture conditions comprises conditions in which the presence of an active thyroidins kinase enzyme in said mammalian cells is required for growth.

5. The method of claim 1, wherein said first selectable polynucleotide expresses an active HPRT enzyme, and said first set of selective culture conditions comprises incubation of said cell in the presence of HAT medium.

6. A method for producing a desired mammalian cell which contains a desired gene sequence inserted within a predetermined gene sequence of said cell's genome, which method comprises:

A. introducing into a mammalian cell a DNA molecule comprising:
   i) said desired gene sequence;
   ii) two regions of homology which flank said desired gene sequence wherein said regions are sufficiently homologous with said predetermined gene sequence to undergo homologous recombination with said predetermined gene sequence of said mammalian cell; and
   iii) at least one selectable gene sequence located within said regions of homology which flank said desired gene sequence wherein presence of least one selectable gene sequence in said mammalian cell can be selected against by culturing said cell under a set of selective culture conditions;

B. permitting said introduced DNA molecule to undergo homologous recombinantion with said predetermined gene sequence of said mammalian cell to produce an intermediate cell, wherein said desired gene sequence has been inserted into said predetermined gene sequence;

C. culturing said intermediate cell thereby permitting said intermediate cell to undergo intrachromosomal recombination or sister chromatid exchange to produce a population of cells;

D. culturing said population of cells under said set of selective culture conditions, wherein said at least one selectable gene sequence is deleted from the genome of the desired mammalian cell; and E. recovering said mammalian cell.

7. The method of claim 6, wherein said mammalian cells are deficient in HPRT enzyme wherein said at least one selectable polynucleotide sequence codes for an active HPRT enzyme, and wherein said first set of selective culture conditions comprises conditions in which the absence of an active HPRT enzyme in said mammalian cells is required for growth.

8. The method of claim 6, wherein said mammalian cells are deficient in APRT enzyme, wherein said at least one selectable polynucleotide sequence codes for an active APRT enzyme, and wherein said first set of selective culture conditions comprises conditions in which the absence of an active APRT enzyme in said mammalian cells is required for growth.

9. The method of claim 6, wherein said mammalian cells are deficient in thyroidine kinase enzyme, wherein said at least one selectable polynucleotide sequence codes for an active thyroidins kinase enzyme, and wherein said first set of selective culture conditions comprises conditions in which the absence or an active thymidine kinase enzyme in said mammalian cells is required for growth.

10. The method of claim 6, wherein said first selectable polynucleotide expresses active HPRT enzyme, and said first set of selective culture conditions comprises incubation of said cell in the presence of 6-thioguantne.

11. A method for producing a desired mammalian cell which contains a desired non-selectable gene sequence inserted within a predetermined gene sequence of said cell's genome, which method comprises:
   A) introducing into a mammalian cell under non-selective culture conditions a DNA molecule comprising:
      i) said desired non-selectable gene sequence;
      ii) two regions of homology which flank said desired nonselectable gene sequence wherein said regions are sufficiently homologous with said predetermined gene sequence to undergo homologous recombination with said predetermined gene sequence of said mammalian cell; and
      iii) at least two selectable gene sequences located within said regions of homology which flank said desired non-selectable gene sequence, wherein the presence of at least one selectable gene sequence in said mammalian cell can be selected for by culturing said mammalian cell under a first set of selective culture conditions, and wherein the presence of least one selectable gene sequence in said mammalian cell can be selected against by culturing said cell under a second set of selective conditions;
   B. permitting said introduced DNA molecule to undergo homologous recombination with said predetermined gene sequence of said mammalian cell to produce an intermediate cell, wherein said desired on-selectable gene sequence has been inserted into said predetermined gene sequence;
   C. recovering said intermediate cell by culturing said intermediate cell under said first set of culture conditions;
   D. culturing said intermediate call under non-selective conditions thereby permitting said intermediate cell to undergo intrachromosomal recombination or sister chromatid exchange or produce a population or cells;
   E. culturing said population of cells under said second set of selective conditions to produce desired mamma cell; and
   F. recovering said desired mammalian cell, wherein said desired mammalian cell has said at least two selectable gene sequences deleted from their genome.

12. The method of claim 11, wherein said mammalian cells are deficient m HPRT enzyme, wherein said at least one selectable polynucleotide sequence codes for an active HPRT enzyme, and wherein said first set of selective culture conditions comprises conditions in which the presence of an active HPRT enzyme in said mammalian cells is required for growth, and wherein said second set of selective culture conditions comprises conditions in which the absence of an active HPRT enzyme in said intermediate cells is required for growth.

13. The method of claim 11, wherein said mammalian cells are deficient in APRT enzyme wherein said at least one selectable polynucleotide sequence codes for an active APRT enzyme, and wherein said first set of selective culture conditions comprises conditions in which the presence of an active APRT enzyme in said mammalian cells is required for growth, and wherein said second set of selective culture conditions comprises conditions in which the absence of an active APRT enzyme in said intermediate cells is required for growth.

14. The method of claim 11, wherein said mammalian cells are deficient in thymidine kinase enzyme, wherein said at least one selectable polynucleotide sequence codes for an active thymidine kinase enzyme, and wherein said first set of selective culture conditions comprises conditions in which the presence of an active thyroidins kinase enzymes in said mammalian cells is required for growth, and wherein said second set of selective culture conditions comprises conditions in which the absence of an active thymidine kinase enzyme in said intermediate cells is required for growth.

15. The method of claim 11, wherein said first selectable polynucleotide expresses an active HPRT enzyme, and first set of selective culture conditions comprises incubation or said cell in the presence of HAT medium, and wherein said second set of selective culture conditions comprises incubation of said coil in the presence of 6-thioguanine.

16. The method of claim 1, 6 or 11, wherein said DNA molecule is introduced into said mammalian cells by subjecting said mammalian cells and said DNA molecule to electroporation.

17. The method of claim 1, 6 or 11, wherein said desired polynucleotide is a human analog of said predetermined sequence of said mammalian cells.

18. A method of producing a desired pluripotent animal cell which contains a desired gene sequence inserted within a predetermined gene sequence of said cell's genome, method comprises:
   A. introducing into a pluripotent animal cell a DNA molecule comprising:
      i) said desired gene sequence:
      ii) regions of homology which flank said gene sequence wherein said regions re sufficiently homologous with said predetermined gene sequence to undergo homologous recombination with said predetermined sequence of said pluripotent animal cell; and
      iii) at least one selectable gene sequence located within said regions of homology which flank said desired gene sequence, wherein presence of at least one selectable gene sequence in said pluripotent animal cell can be selected for by culturing said under a set of selective culture conditions;
   B. permitting said introduced DNA molecule to undergo homologous recombination with said predetermined gene sequence of said Pluripotent animal cell to produce an intermediate cell, wherein said desired gene sequence has been inserted into said predetermined gene sequence;
   C. recovering said intermediate cell by culturing said intermediate cell under said selective culture conditions;
   D. culturing said intermediate cell under conditions such that said intermediate cell undergoes intrachromosomal recombination or sister chromatid exchange, wherein said at least one selectable gene sequence is deleted from the cell's genome and said desired pluripotent animal cell is produced;

E. recovering said desired pluripotent animal cell.

19. The method of claim 18, wherein said pluripotent animal cells are deficient in HPRT enzyme, wherein said at least one selectable polynucleotide sequence codes for an active HPRT enzyme, and wherein said first set of selective culture conditions comprises conditions in which the presence of an active HPRT enzyme in said pluripotent animal cells is required for growth.

20. The method of claim 18, wherein said pluripotent animal cells are deficient in APRT enzyme, and wherein said at least one selectable polynucleotide sequence codes for an active APRT enzyme, and wherein said first set of selective culture conditions comprises conditions in which the presence of an active APRT enzyme in said pluripotent animal cells is required for growth.

21. The method of claim 18, wherein said pluripotent animal cells are deficient in thymidine kinase enzyme, wherein said at least one selectable polynucleotide sequence culture for an active thyroidins kinase enzyme, and wherein said first set of selective culture conditions comprises conditions in which the presence of an active thyroidine kinase enzyme in said pluripotent animal cells is required for growth.

22. The method of claim 18, wherein said first selectable polynucleotide expresses an active HPRT enzyme, and said first set of selective culture conditions comprises incubation or said cell in the presence of HAT medium.

23. A method of introducing a desired pluripotent animal cell which contains a desired gene sequence inserted within a predetermined gene sequence of said cell's genome, which method comprises:

A. introducing into a pluripotent animal cell a DNA molecule comprising:
   i) said desired gene sequence;
   ii) two regions of homology which flank said desired gene sequence wherein said regions are sufficiently homologous with said predetermined gene sequence to undergo homologous recombination with said predetermined gene sequence of said pluripotent animal cell; and
   iii) at least one selectable gene sequence located within said regions of homology which flank said desired non-selectable gene sequence, wherein the presence of least one selectable gene sequence in said pluripotent animal cell can be selected against by culturing said cell under a set of selective culture conditions;

B. permitting said introduced DNA molecule to undergo homologous recombination with said pluripotent animal cell to produce an intermediate cell, wherein said desired gene sequence has been inserted into said predetermined gene sequence;

C. culturing said intermediate cell thereby permitting said intermediate cell to undergo intrachromosomal recombination or sister chromatid exchange or produce a population of cells;

D. culturing said population of cells under said set of selective culture conditions, wherein said at least one selectable gene lens sequence is deleted from the genome of the desired mammalian cell, and E. recovering said desired pluripotent animal cell.

24. The method of claim 23, wherein said pluripotent animal cells are deficient in HPRT enzyme, wherein said at least one selectable polynucleotide sequence codes for an active HPRT enzyme, and wherein said first set of selective culture conditions comprises conditions in which the absence of an active HPRT enzyme in said pluripotent animal of cells is required for growth.

25. The method of claim 23, wherein said pluripotent animal cells are deficient in APRT enzyme, wherein said at least one selectable polynucleotide sequence codes for an active APRT enzyme, and wherein said first set of selective culture conditions comprises conditions in which the absence of an active APRT enzyme in said pluripotent animal cells is required for growth.

26. The method of claim 23, wherein said pluripotent animal cells are deficient in thymidine kinase enzyme, wherein said at least one selectable polynucleotide sequence codes for an active thyroidins kinase enzyme, and wherein said first set of selective culture conditions comprises conditions in which the absence of an active thymidine kinase enzyme in said pluripotent animal cells is required for growth.

27. The method of claim 23, wherein said first selectable polynucleotide expresses an active HPRT enzyme, and said first set of selective culture conditions comprises incubation or said cell in the presence of 6-thioguanine.

28. A method for producing a desired pluripotent cell which contains a desired non-selectable gene sequence inserted within a predetermined gene sequence of said cell's genome, which method comprises:

A introducing into a pluripotent animal cell under non-selective culture conditions a DNA molecule comprising:
   i) said desired non-selectable gene sequence:
   ii) two regions of homology which flank said desired nonselectable gene sequence wherein said regions are sufficiently homologous with said predetermined gene sequence to undergo homologous recombination with said predetermined gene sequence of said mammalian cell; and
   iii) at least two selectable gene sequences located within said regions homology which flank said desired non-selectable gone sequence, wherein the presence of at least one selectable gene sequence in said mammalian cell can be selected for by culturing said mammalian cell under a first set or selective culture conditions, can be selected against by culturing said cell under a second set of selective conditions;

B. permitting said introduced DNA molecule to undergo homologous recombination with said predetermined gene sequence of said pluripotent animal cell to produce an intermediate cell, wherein said desired non-selectable gene sequence has been inserted into said predetermined gene sequence;

C. recovering said intermediate cell by culturing said intermediate cell under said first set of culture conditions;

D. culturing said intermediate cell under non-selective conditions thereby permitting said intermediate cell to undergo intrachromosomal recombination or sister chromatid exchange or produce a population of cells;

E. culturing said population of cells under said second set of selective conditions to produce said desired pluripotent animal cell; and F. recovering said desired pluripotent animal cell, wherein said desired pluripotent animal cell has said at least two selectable gene sequences deleted from their genome.

29. The method of claim 28, wherein said pluripotent animal cells are deficient in HPRT enzyme, wherein said at least one selectable polynucleotide sequence codes for an active HPRT enzyme, and wherein said frost set of selective culture conditions comprises conditions in which the presence of an active HPRT enzyme in said pluripotent animal cells is required for growth, and wherein said second set of selective culture conditions comprises conditions in which the absence of an active HPRT enzyme in said intermediate cells is required for growth.

30. The method of claim 28, wherein said pluripotent animal cells are deficient in APRT enzyme, wherein said at least one selectable polynucleotide sequence codes for an active APRT enzyme, and wherein said first set of selective culture conditions comprise conditions in which the presence of an active APRT enzyme in said pluripotent animal cells is required for growth, and whereto said second set of selective culture conditions comprises conditions in which the absence of an active APRT enzyme in said intermediate cells is required for growth.

31. The method of claim 28, wherein said pluripotent animal cells are deficient in thymidine kinase enzyme, wherein said at least one selectable polynucleotide sequence codes for an active thyroidins kinase enzyme, and wherein said first set of selective culture conditions comprises conditions in which the presence of an active thyroidine kinase enzyme in said pluripotent animal cells is required for growth, and wherein said second set of selective culture conditions comprises conditions in which the absence of an active thyroidins kinase enzyme in said intermediate cells is required for growth.

32. The method of claim 28, wherein said first selectable polynucleotide expresses an active HPRT enzyme, and said first set of selective culture conditions comprises incubation of said pluripotent animal cell in the presence of hypoxanthine, and wherein said second set of selective culture conditions comprises incubation of said intermediate cell in the presence of 6-thioguanine.

\* \* \* \* \*